United States Patent [19]
Shih et al.

[11] Patent Number: 6,151,970
[45] Date of Patent: Nov. 28, 2000

[54] VIRTUAL CYCLONE SAMPLER

[75] Inventors: Tung-Sheng Shih; Chih-Chieh Chen; Sheng-Hsiu Huang, all of Taipei, Taiwan

[73] Assignee: Institute of Occupational Safety and Health, Council of Labor Affairs, Executive Yuan, Taipei, Taiwan

[21] Appl. No.: 09/327,176

[22] Filed: Jun. 7, 1999

[51] Int. Cl.$^7$ ................................................ G01N 1/00
[52] U.S. Cl. .......................................................... 73/863.22
[58] Field of Search ........................... 73/863.21, 863.22, 73/28.04, 28.05, 28.06; 55/337, 345, 447; 210/512.2

[56] References Cited

U.S. PATENT DOCUMENTS 5,277,705   1/1994   Anderson et al. ........................ 55/345
5,437,198   8/1995   John ..................................... 73/863.22

FOREIGN PATENT DOCUMENTS 3110871   10/1982   Germany ............................. 73/28.05

*Primary Examiner*—Robert Raevis
*Attorney, Agent, or Firm*—Bacon & Thomas, PLLC

[57] ABSTRACT

A virtual cyclone sampler of a hollow rectangular container is provided with an arcuate surface by chamfering an edge thereof. The virtual cyclone sampler is further provided with two guide slots which are located at junctions of the arcuate surface and two adjacent planes sharing the chamfered edge. The guide slots are intended to guide gas or airborne particles to flow into or out of the container. Two virtual cyclone samplers may be connected in symmetry to form a composite virtual cyclone sampler.

12 Claims, 20 Drawing Sheets

VIRTUAL CYCLONE SAMPLER

FIELD OF THE INVENTION

The present invention relates to a virtual cyclone sampler.

BACKGROUND OF THE INVENTION

The agreement jointly reached by American Conference of Governmental Industrial Hygienists (ACGIH), International Standards Organization (ISO) and Comite Europeen de Normalisation (CEN) is generally accepted as a new standard for the health-related aerosol size-selective sampling. The agreement includes a new definition of a respirable aerosol, which is in fact a compromise between the two definitions given by British Medical Research Council (BMRC) and American Conference of Governmental Industrial Hygienists (ACGIH). As far as 50% cut-off diameter is concerned, it is set respectively by BMRC and ACGIH (1985) as 5 $\mu$m and 3.5 $\mu$m, with the newest one being 4 $\mu$m set by ISO/CEN/ACGIH. As far as the slope of the penetration curve, the newest definition is milder than the two old definitions.

The 10 mm nylon cyclone and the SKC cyclone are most commonly used in Taiwan for sampling the respirable particles. According to the research report [Bartley et al., Am. Ind. Hyg. Assoc. J., 55(11): 1034–1046, 1994], these two cyclone samplers can conform to the standard set forth by ACGIH/ISO/CEN by means of an appropriate flow-rate adjustment. However, the inclinations of their penetration curves are steeper than the inclination of the international newest convention curve. For this reason, there will be an underestimation and an overestimation with regard to the greater and the smaller particles at the time when the sampling is actually carried out. There was a research report to the effect that the overestimation and the underestimation can cancel out each other, and that the sampling error may not be too great. However, under the circumstance that the aerosol distribution is extreme, the sampling error may be rather considerably serious. In light of this, Gautam and Sreenath derived an improved multi-inlet cyclone from a 10 mm nylon cyclone in 1997. According to the test results, its penetration curve has a slope and 50% cut-off diameter, which are more closer to those of the convention curve. In addition, the errors resulting from the sampling direction is reduced.

The design of the cyclone sampler is based on the vortex as well as the principle of inertia impact. The particles are likely to deposit, trip, slide and even roll at the moment when the particles are thrown by the centrifugal force to make contact with the tube wall, depending on the characteristics of the particles and the tube wall. This implies that the separation efficiency curve of the particles may deviate due to the load of particles. With regard to the problem of dust load in the cyclone, it was found by Blachmann and Lippman that the solid particles were gradually deposited on the inner wall opposite to the inlet of the 10 mm nylon cyclone. Please refer to Blachman, M. W. and Lippman, M., Am. Ind. Hyg. Assoc. J., 35: 311–326, 1974. As a result of the particle deposition, the effective radius of the cyclone is reduced, thereby resulting in an improvement on the particle collecting efficiency. As the particles are accumulated to have a considerable thickness, an avalanche is likely to take place to result in an increase in the effective radius of the cyclone once again. As a result, the particle-collecting efficiency is once again lowered. However, they neither quantify the problem nor propose solutions to the problem. In order to cope with the problem as described above, a new BB cyclone was disclosed. The BB cyclone is made of an aluminum alloy material conductive to electricity, and has a greater inner diameter and an exit tube length for reducing the particle deposition on the inner wall as well as the impact of the particle load on the collection efficiency. However, the BB cyclone is similar in pattern and principle to the conventional cyclone such that the particle deposition also takes place in the BB cyclone, and that the effective radius of the BB cyclone is decreased, and further that the separation efficiency curve of the BB cyclone is affected by the particle load.

The aerosol that is inhaled through the respiratory duct may be deposited in the body tissue due to the action of various depository mechanisms, such as gravity sinking, diffusion, static, impact and interception. Moreover, the inhaled aerosol may be exhaled. The aerosol deposited in the respiratory duct can not be easily removed and may be responsible for various disorders of the respiratory system. The removal rate of the aerosol that is deposited in the respiratory system varies from one part to another of the respiratory system. For this reason, the amount of aerosol deposit and the body part in which the aerosol is deposited are two important factors that must be taken into consideration in terms of the relationship between the health and the aerosol. The conventional method for sampling aerosol at the work site is based on the total aerosol and is therefore insufficient to meet the actual requirements of the investigation.

For the convenience of investigating the health relationship between the aerosol and the human body, the human respiratory system may be divided into three groups, which include head (mouth, throat, nostrils, etc.), bronchus (trachea, or windpipe), and lung (pulmonary alveolus, pleura).

The aerosol with a greater diameter is often intercepted and deposited in the nose. The aerosol deposited in head and bronchus may be removed by means of flagellation. The aerosol with a smaller diameter is prone to deposit in the pulmonary vesicle and can be removed therefrom only by phagocyte. The ingestion of aerosol by the phagocyte is less efficient than the removal of aerosol by the flagellation. In light of the reasons stated above, it is necessary to develop the so-called "size-selective sampler" for measuring the concentration of the aerosol that is deposited in a specific portion of the respiratory system. The size-selective sampler is based on the ideal size-selective standard in which the aerodynamic diameter of aerosol is used as a function.

In the past ten years, the use of the aerosol size-selective sampler involved the respirable standard suggested by BMRC (British Medical Research Council). However, ISOC (International organization for standardization) suggested in 1985 the evaluation standards which include the inhalable standard, the thoracic standard, and the alveolar standard. In the same year, ACGIH came up with the standards which were basically similar to ISOC's standards. In other words, there are so many standards that were suggested by various organizations. None of these standards is internationally accepted.

Three fractions of size-selective sampling suggested by Sidney C. Soderholm in 1989 are currently accepted by ACGIH, ISO, CEN (Commite Europeen de Normalisation) and NIOSH. For more details, plese refer to Soderholm S. C., Ann. Occup. Hyp. 33 (3), 303–320, 1989. The three size-selective sampling methods are described hereinafter.

1. Inspirable or inhalable fraction

The size-selective sampling efficiency curve of the inspirable or inhalable fraction is a continuation of the standard suggested by ACGIH in 1985.

Inhalable fraction:

$$SI(d)=50\%*(1+e^{-0.06d}) \quad (1)$$

$0<d<=100 \ \mu m$

SI(d): collection efficiency of inhalable fraction sampler at the time when aerodynamic diameter is d $\mu$m.

This is based on the disclosure by Vincent & Armbruster in 1981, who compiled the data of the research in which the inhaling of aerosol through mouth and nose of the human head model was studied in the wind hole. The international standards adopt the concept of inhalable aerosol and add this fraction for the possibility of aerosol deposition in mouth, throat, and nostrils.

2. Thoracic fraction

According to Yu et al., 1981; Miller et al., 1988; Heyder et al., 1986; Rudolf et al., 1988 (Heyder, J. et al., J. Aerosol Sci., 17: 811–825, 1986 and Rudolf, G., J. Aerosol Med., 1:209–210, 1988), the data can be inferred on the basis of the theory that the fraction is deposited in the respiratory duct by taking the actual sampling efficiency into consideration. As a result, the thoracic fraction was defined as follows:

Thoracic fraction:

$$ST(d)=SI(d)*\{1-F(x)\} \quad (2)$$

$X=\{\ln(d/\Gamma)\}/\{\ln(\Sigma)\}$
$\Gamma=11.64 \ \mu m$
$\Sigma=1.5$

ST: sampling efficiency of the thoracic fraction sampler
F(x)=cumulative probability function of the standardized variable x $$F(x) = \int_{-\infty}^{x} \frac{dx}{\sqrt{2\pi}} e^{-x^2/2}$$

The numerical method for computing he value of F(x) is as follows:

$$y = \left| \frac{x}{\sqrt{2\pi}} \right| \quad (4)$$

$$G(y)=0.5(1+0.14112821y+0.08864027y^2+0.02743349y^3- 0.0039446y^4+0.00328975y^5)^{-8} \quad (5)$$

When $-4<Y<4$, the absolute error is smaller than $\pm 0.0001$.

3. Respirable fraction

According to Milleret et al., 1988; Heyder et al., 1986 (Please refer to the references cited above); Lippmann & Albert, 1969; Chan & Lippmann, 1980; and Heyder et al., 1986, the studies were done on the aerosol deposit in the bronchus and the alveolus. They also took the actual sampling efficiency of the sampler into consideration when they defined the standard.

Respirable fraction:

$$SR(d)=SI(d)*\{1-F(x)\} \quad (6)$$

F(X) is the same as above
$\Gamma=4.25 \ \mu m$
$\Sigma=1.5$

The conventional size-selective sampler is based on the principle of the aerosol inertia. The aerosol of a large diameter and the aerosol of a small diameter are separated by an impact device or a cyclone.

SUMMARY OF THE INVENTION

A virtual cyclone sampler constructed in accordance with the present invention comprises a container of a hollow rectangular body having one edge which is chamfered to form an arcuate surface. The arcuate surface and two chamfered planar surfaces form two junctions, each having a guide slot for guiding the atmospheric air or aerosol into or out of the container.

Alternatively, two virtual cyclone samplers of the present invention can be used to form a composite virtual cyclone sample, wherein said two virtual cyclone samplers are connected in symmetry such that two guide slots of said two virtual cyclone samplers are connected with each other, and thus said hollow rectangular or like rectangular bodies of said two virtual cyclone samplers are in communication with one another through said two connected guide slots.

Preferably, said two guide slots of the virtual cyclone sampler are rectangular slits conforming to said hollow rectangular body.

Preferably, one of said two guide slots of the virtual cyclone sample is provided with a protruded wall circumventing said rectangular slits. Preferably, said rectangular silts have a depth equal to a depth of said hollow rectangular body, and a width ($W_i$, $W_o$) ranging between 0.4 and 1.6 mm, more preferably between 0.5 to 1.2 mm, and most preferably between 0.6 to 1.0 mm.

Preferably, said hollow rectangular body of the virtual cyclone sampler has a length (L) ranging between 10 and 100 mm, more preferably between 13 and 92 mm, and most preferably between 15 to 25 mm; and a width (W) ranging between 10 and 100 mm, more preferably between 13 and 92 mm, and most preferably between 15 to 25 mm.

Preferably, said arcuate surface of the virtual cyclone sampler has a radius (R) ranging between 5 and 25 mm, more preferably between 7.5 to 19 mm, and most preferably between 8 to 12 mm; and said radius is smaller than the length (L) and the width (W) of said hollow rectangular body.

Preferably, said length (L) of said hollow rectangular body is equal to said width (W) of said hollow rectangular body of the virtual cyclone sampler.

The virtual cyclone sampler of the present invention is also based on the principle of aerosol inertia. However, the virtual cyclone sampler of the present invention is different in design in that the aerosol is confined in a rectangular container after the aerosol is separated from the main gas flow field by the inertia force. The confined aerosol may float or precipitate in the rectangular container. However, the aerosol is not captured by its direct impact on the walls of the rectangular container. As a result, the effective radius is not involved, and thus the size-selective sampling efficiency curve is not affected by the load of the aerosol in the virtual cyclone sampler of the present invention.

Gibson and Vincent (Gibson, H and Vincint, J. H., Ann. Occup. Hyg. 24 (2): PP205–215, 1981) proposed that a front size-selective sampler must be light in weight, compact, and durable, so that the sampler is suitable for a subject to wear, and further that the sampler must have a low resistance. The virtual cyclone sampler of the present invention conforms to all conditions described above.

The features, functions, and advantages of the present invention will be more readily understood upon a thoughtful deliberation of the following detailed description of the preferred embodiments of the present invention with reference to the accompanying drawings.

BRIEF DESCRIPTION OF THE DRAWINGS

Figure 3:
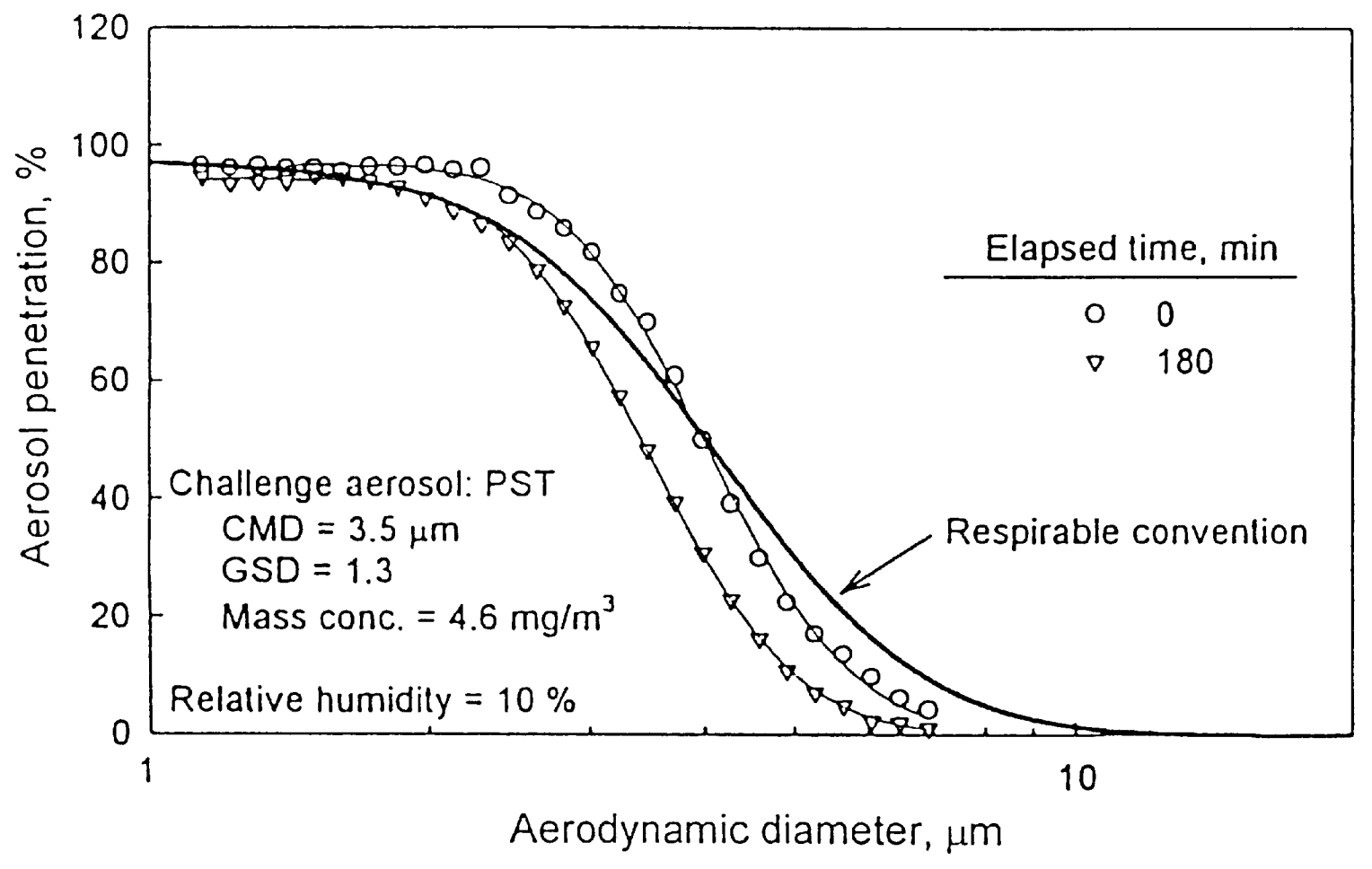

FIG. 3 shows aerosol penetration curves which are obtained at the beginning and after 3-hour lapsed time of sampling by using the prior art nylon cyclone. size-selective sampler.

Figure 4:
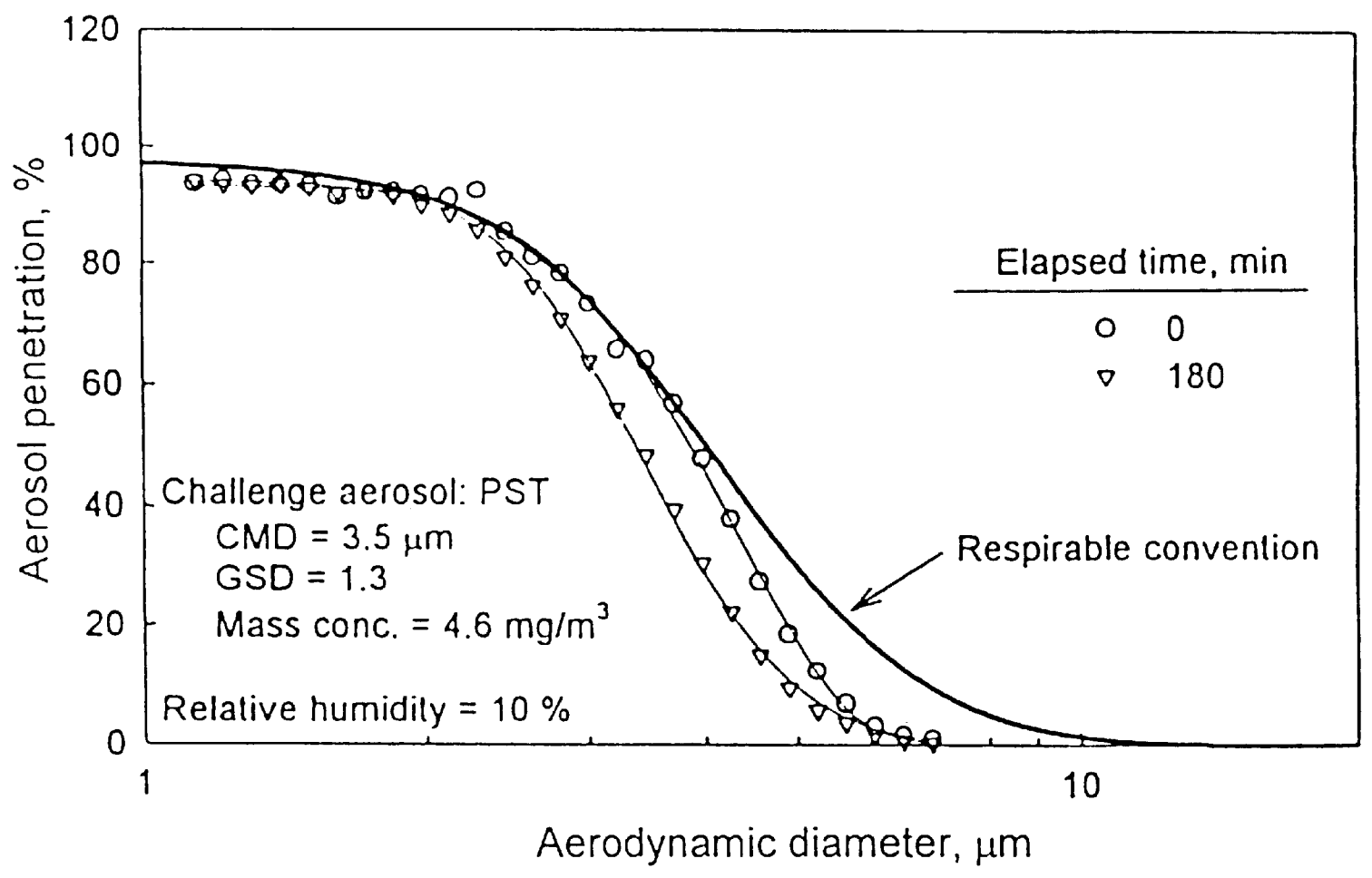

FIG. 4 shows aerosol penetration curves which are obtained at the beginning and after 3-hour lapsed time of sampling by using the prior art SKC cyclone size-selective sampler.

Figure 6:
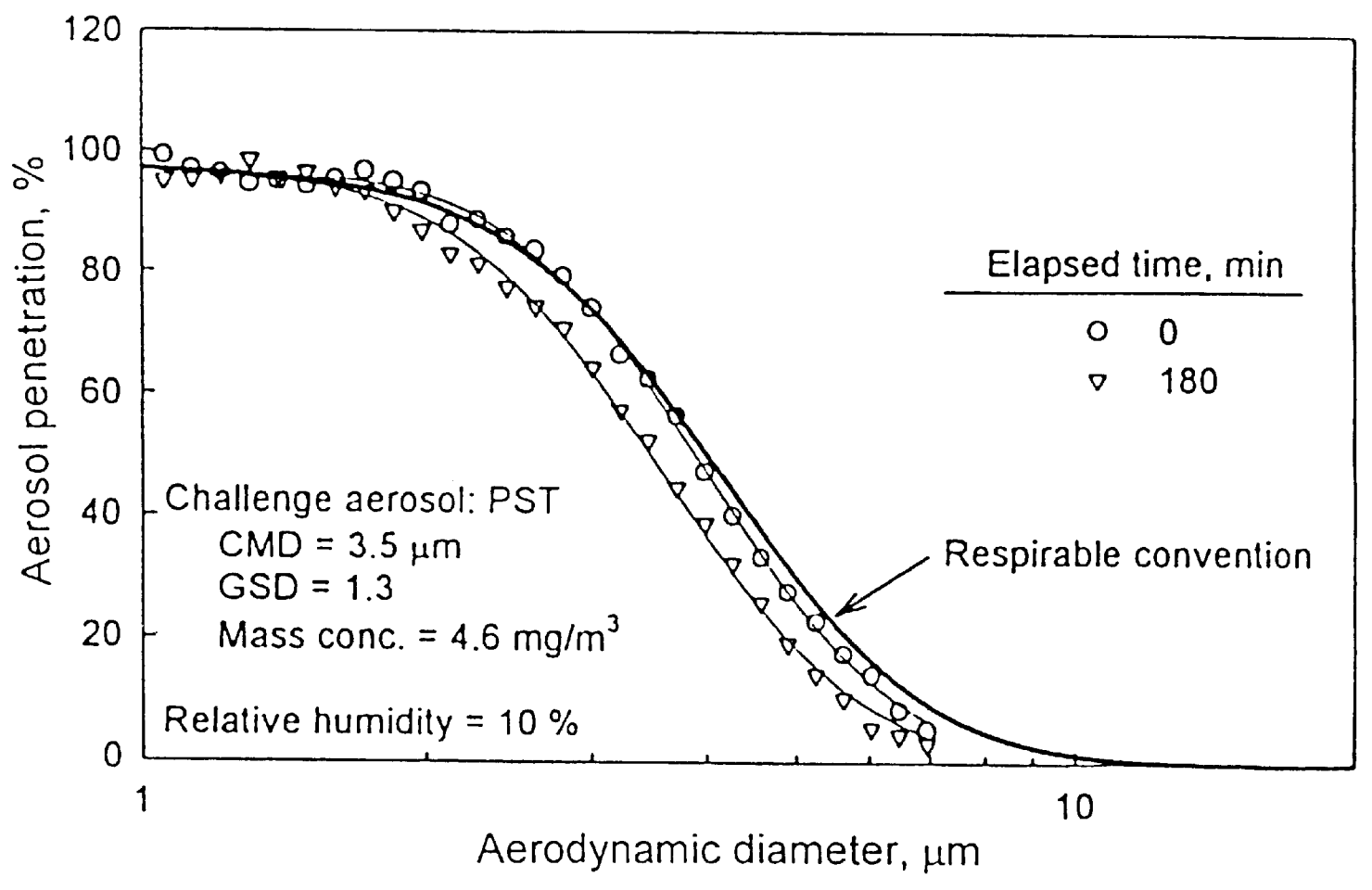

FIG. 6 shows aerosol penetration curves which are obtained at the beginning and after 3-hour lapsed time of sampling by using the prior art multi-port cyclone size-selective sampler.

FIGS. 9–12 are aerosol penetration (%) vs. aerodynamic diameter ($\mu$m) plots showing aerosol penetration curves of the preferred embodiments 1–11 of the present invention.

FIG. 13 is an aerosol penetration (%) vs. aerodynamic diameter ($\mu$m) plot showing aerosol penetration curves of the preferred embodiment 12 of the present invention.

FIG. 14 is an aerosol penetration (%) vs. elapsed time (min) plot showing the changes in penetration rate of particles having an aerodynamic diameter ($D_{ae}$) of 3.97 along with the elapsed time in the preferred embodiment 13 of the present invention.

FIG. 15 is an aerosol penetration (%) vs. aerodynamic diameter ($\mu$m) plot showing aerosol penetration curves of the preferred embodiment 13 of the present invention.

FIG. 16 is an aerosol penetration (%) vs. elapsed time (min) plot showing the changes in penetration rate of particles having an aerodynamic diameter ($D_{ae}$) of 3.97 along with the elapsed time in the preferred embodiment 13 of the present invention.

Figure 18:
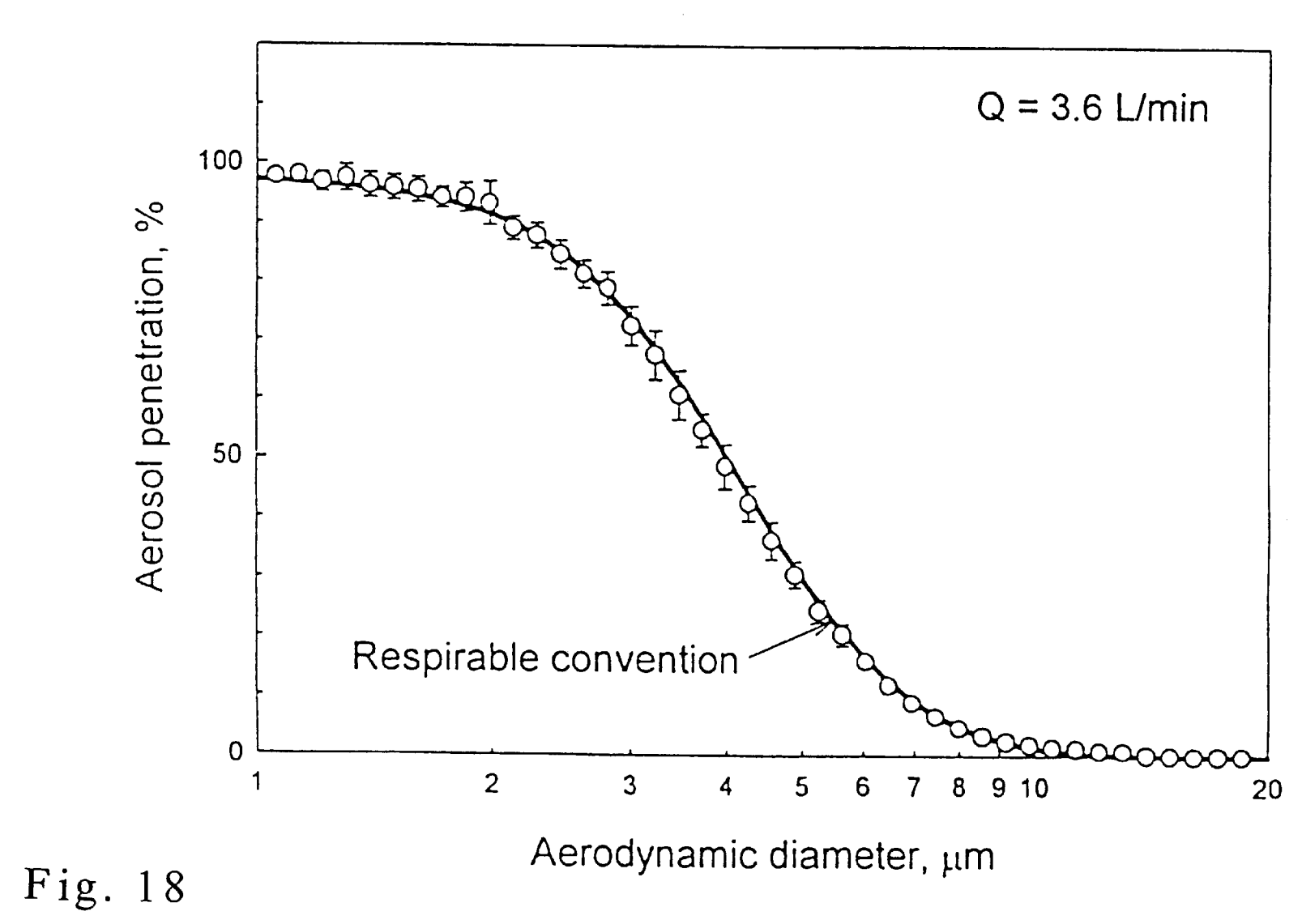

FIG. 18 shows an aerosol penetration curve of the composite virtual cyclone sampler shown in FIG. 17.

Figure 19:
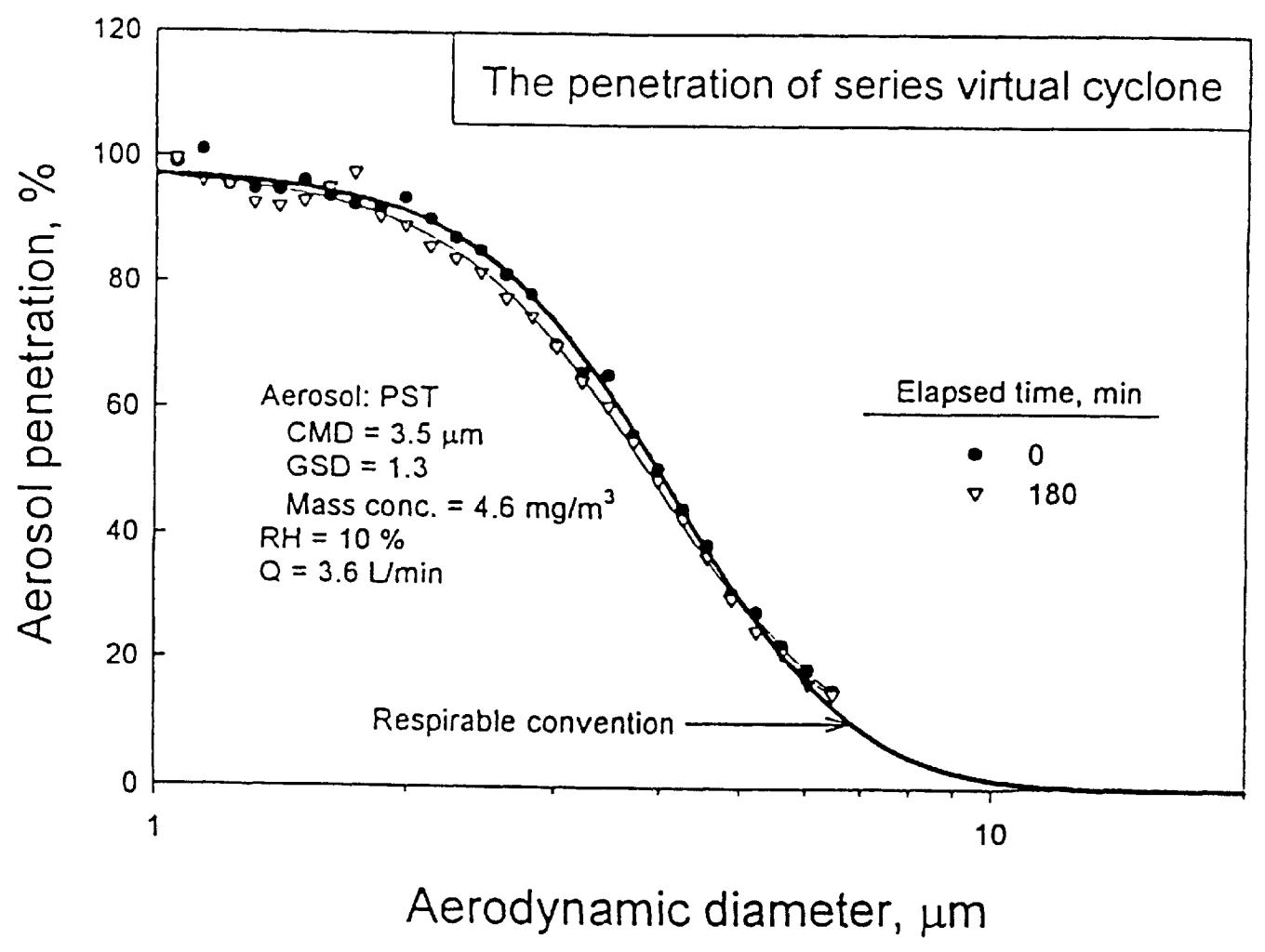

FIG. 19 is an aerosol penetration (%) vs. aerodynamic diameter ($\mu$m) plot showing aerosol penetration curves of the preferred embodiment 15 of the present invention.

Figure 20:
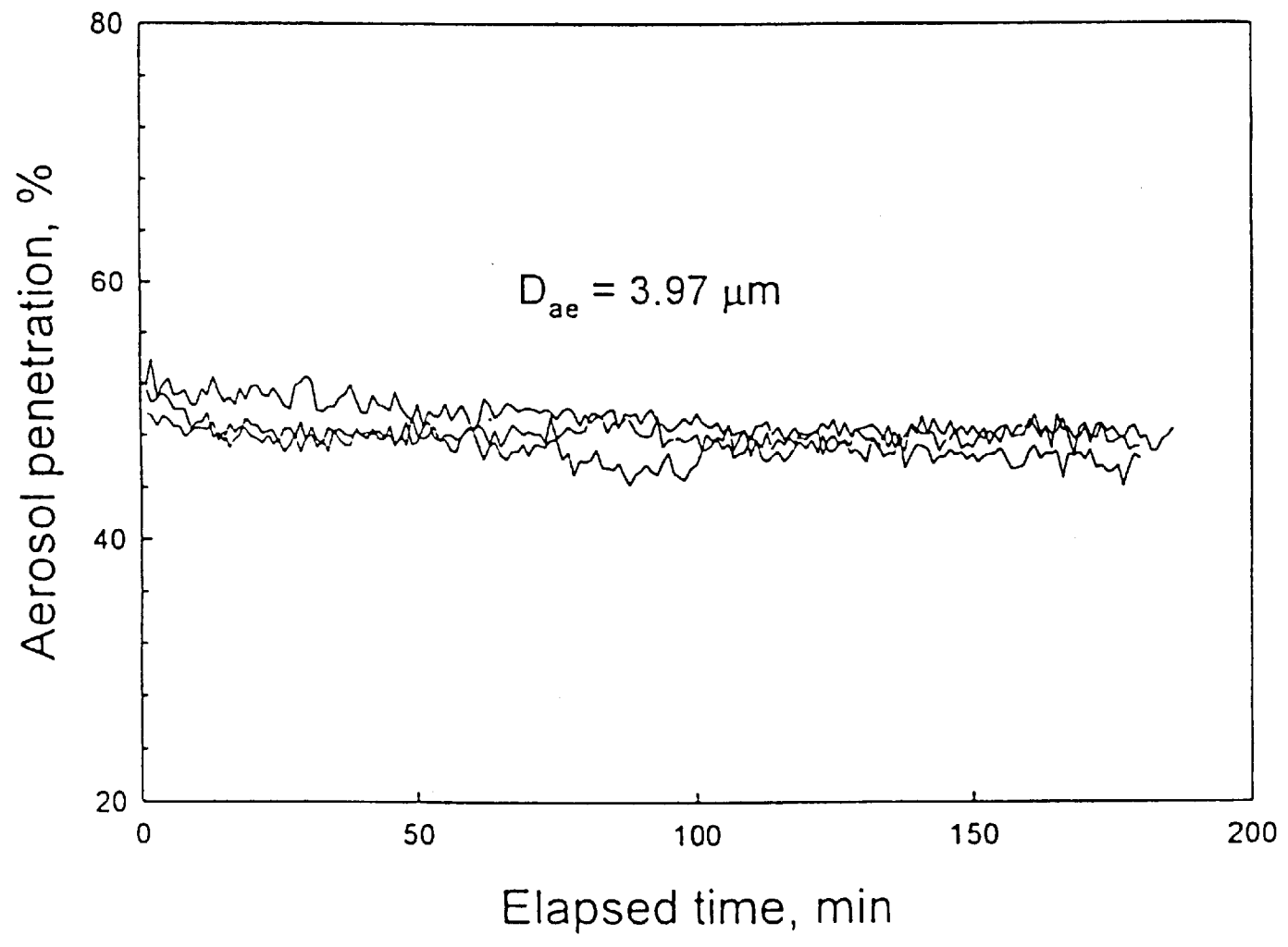

FIG. 20 is an aerosol penetration (%) vs. elapsed time (min) plot showing the changes in penetration rate of particles having an aerodynamic diameter ($D_{ae}$) of 3.97 along with the elapsed time in the preferred embodiment 15 of the present invention.

DETAILED DESCRIPTION OF THE INVENTION

The virtual cyclone sampler of the present invention is a hollow rectangular body or like rectangular container having a curved surface in place of a side edge. The curved surface is an arcuate surface or like arcuate surface. The arcuate surface and two chamfered surfaces have two junctions, each having a guide slot serving as a passage of gas or aerosol into or out of the container.

Figure 1:
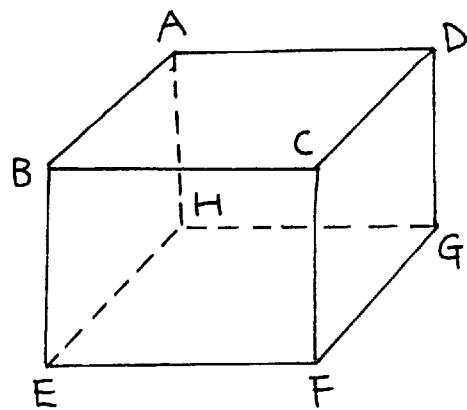
FIGS. 1 and 2 show schematic views of a rectangular body, an edge and an arcuate surface defined in the present invention.

The so-called "rectangular body" is a rectangular body in mathematical sense. As shown in FIG. 1, the rectangles ABCD and EFGH, ABEH and CFGD, BCFE and ADGH are parallel to each other. The rectangles ABEH, BCFE, CDGF and ADGH are respectively perpendicular to the rectangle ABCD, as well as the rectangle EFGH. The so-called "like rectangular body" refers to the above parallel planar surfaces being approximately parallel to each other, and the above perpendicular planar surfaces being approximately perpendicular to each other. The rectangles ABCD, ABEH, BCFE, CDGF, ADGH and EFGH may be approximately rectangular tetragons, or even close to the curved surface of the planar surface. The so-called "side edge" referred to above is meant to indicate the boundary edge of two adjoining surfaces. For example, the section CD at the boundary between the rectangle ABCD and the rectangle CDGF in FIG. 1 is the side edge.

Figure 2:
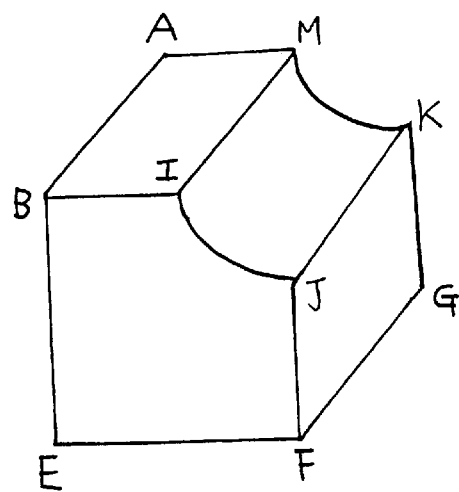
Figure 5:
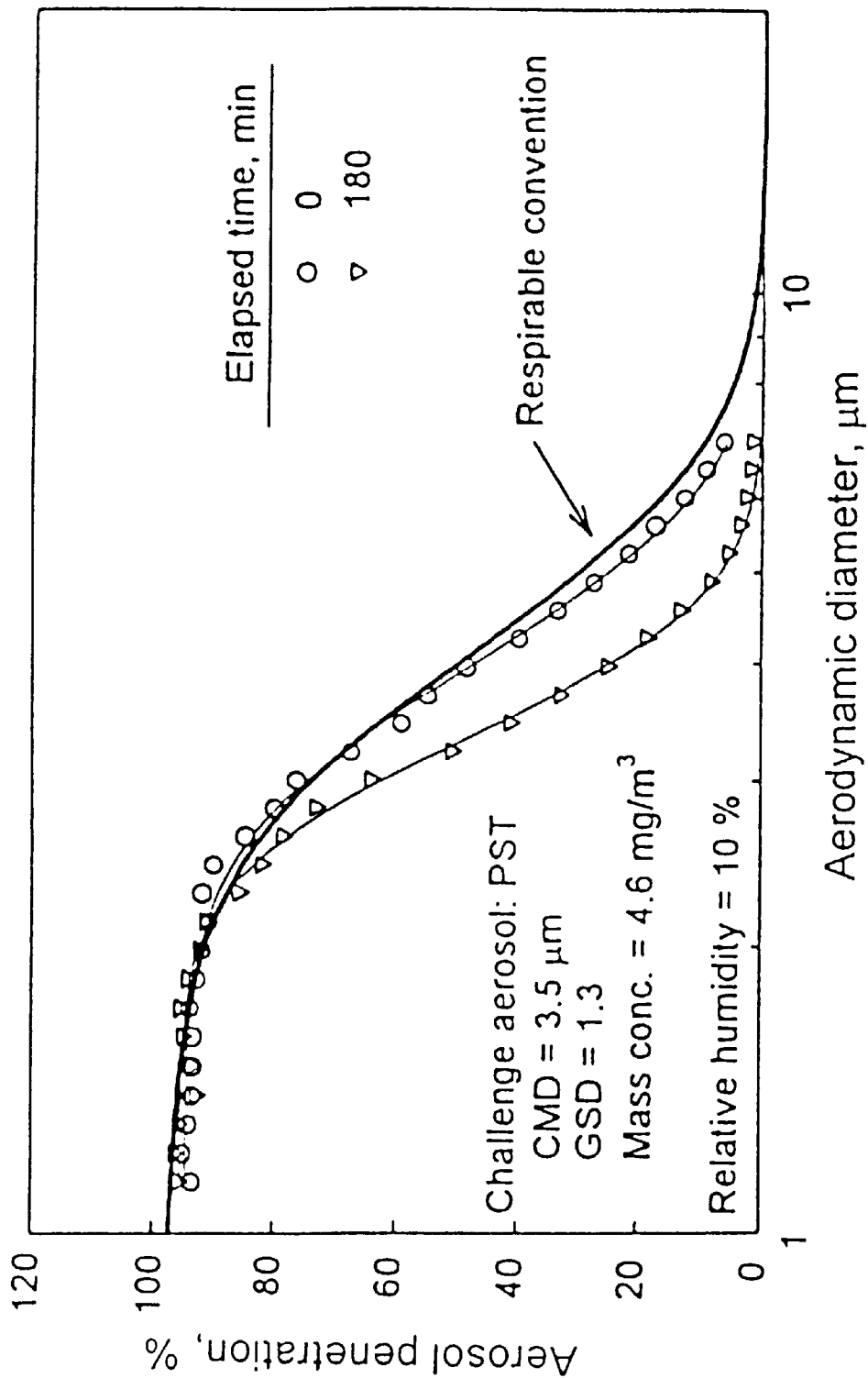
FIG. 5 shows aerosol penetration curves which are obtained at the beginning and after 3-hour lapsed time of sampling by using the prior art BB cyclone size-selective sampler.

The so-called "arcuate surface" refers to a partial surface located between two intersecting planes parallel to the axis of a cylinder, such as the curved surface IJKM in FIG. 2. The so-called "like arcuate surface" refers to a curved surface similar in shape to an arcuate surface, such as an oblong curved surface, a parabolic curved surface, etc. The so-called "two chamfered surfaces" referred to above are the planes ABIM and JFGK, as shown in FIG. 2. The so-called "junctions" referred to above are the sections IM and JK, as shown in FIG. 2.

The container referred to above is preferably a rectangular container having an arcuate curved surface in place of a side edge. The arcuate surface is preferably one quarter of a curved surface of a cylinder, such as the arcuate surface IJKM in FIG. 2, which is one quarter of a curved surface of a cylinder having a section CD (shown in FIG. 1) as an axis. The rectangles BCFE and ADGH of FIG. 1 are preferably square in shape.

The above container has a depth corresponding to a length AB in FIG. 1. The depth is not specifically limited and is dependent on the magnitude of the sampling flow rate. To be more specific, the depth is directly proportional to the magnitude of the sampling flow rate.

Figure 7:
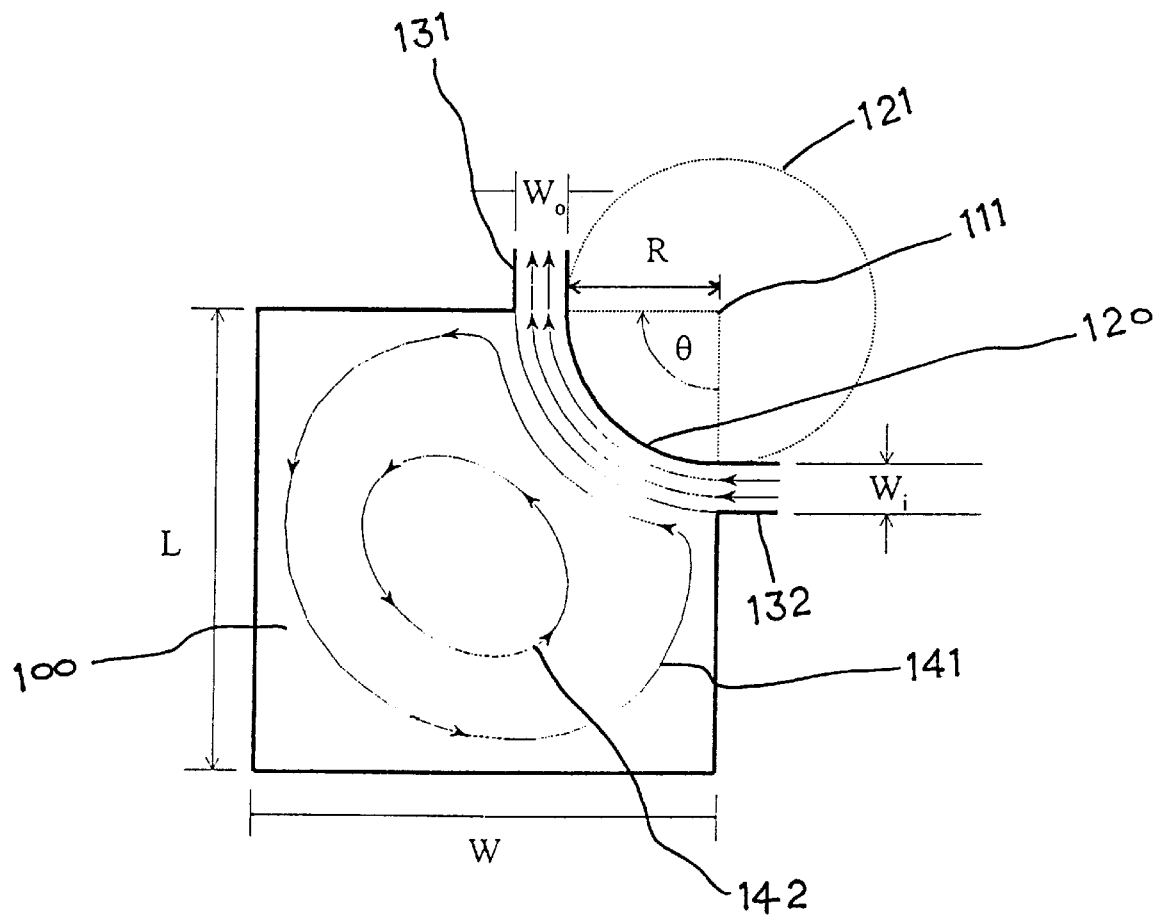
FIG. 7 shows a sectional view of a virtual cyclone sampler of the present invention and a schematic view of stream lines of the air flow.
Figure 21:
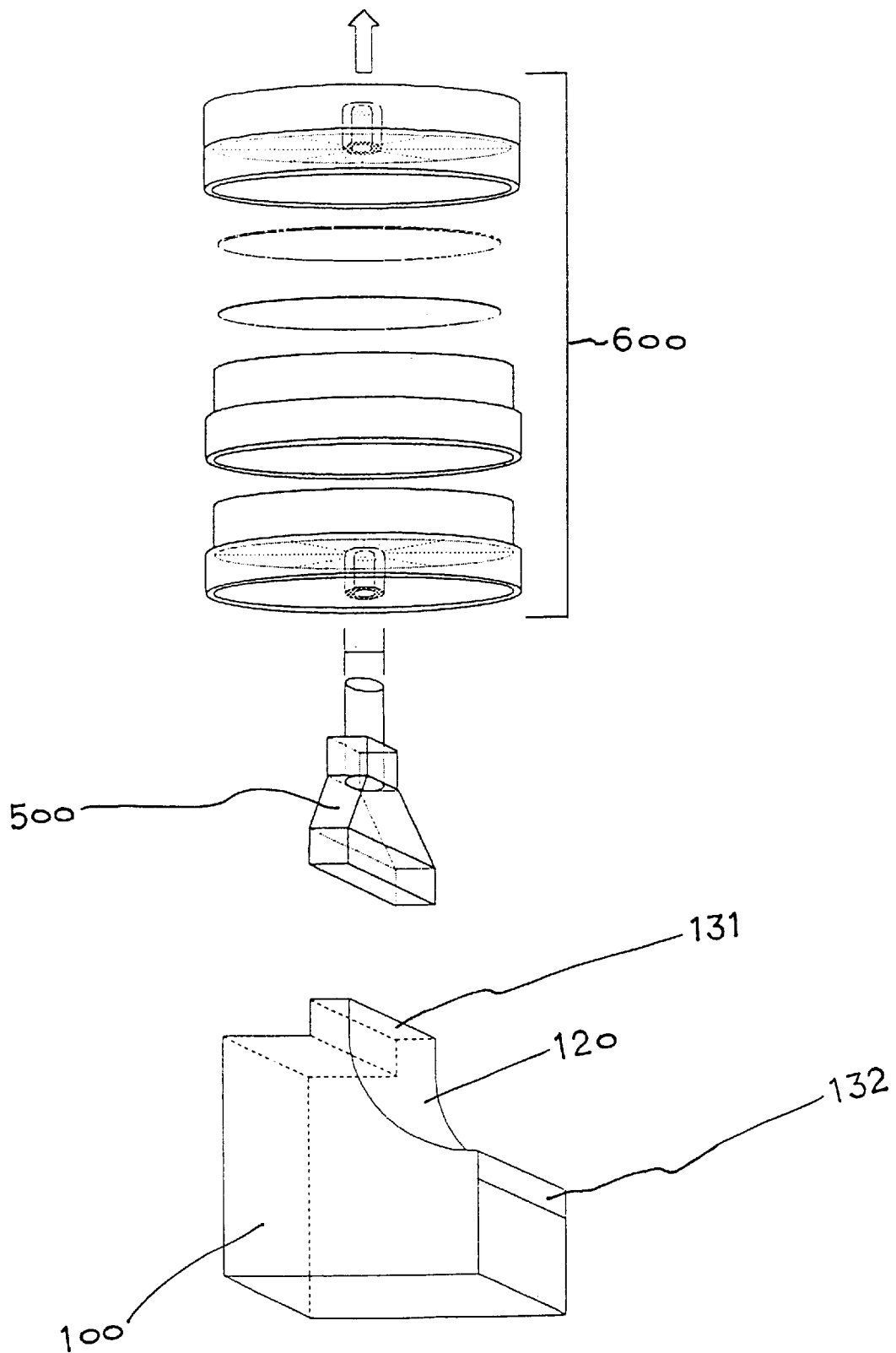
FIG. 21 is a schematic view showing the mounting of a filter cassette to the virtual cyclone sampler of the present invention.

The guide slot of the present invention may be a simple opening or a protruded guide slot, as shown in FIG. 7. Preferably, there is at least one protruded guide slot for connecting an outside component, such as a filter cassette, as shown in FIG. 21.

As shown in FIG. 7, a virtual cyclone sampler embodied in the present invention comprises a rectangular container 100 having an arcuate surface 120, and two protruded guide slots 131 and 132 which are located at the junctions of the arcuate surface 120 and the two chamfered surfaces. The two protruded guide slots 132 and 131 are used to guide the gas into and out of the container 100, respectively. The air stream lines in the virtual cyclone sampler are denoted by 141 and 142. In FIG. 7, the side edge 111 is replaced by the arcuate surface 120. The dotted line 121 refers to the cylinder forming the arcuate surface 120. The letters "R" denotes the radius of the arcuate surface; $\theta$, the angle of the side edge 111; $W_i$, the width of the guide slot 132; $W_o$, the width of the guide slot 131; L, the length of the virtual cyclone sampler; and W, the width of the virtual cyclone sampler.

Figure 8:
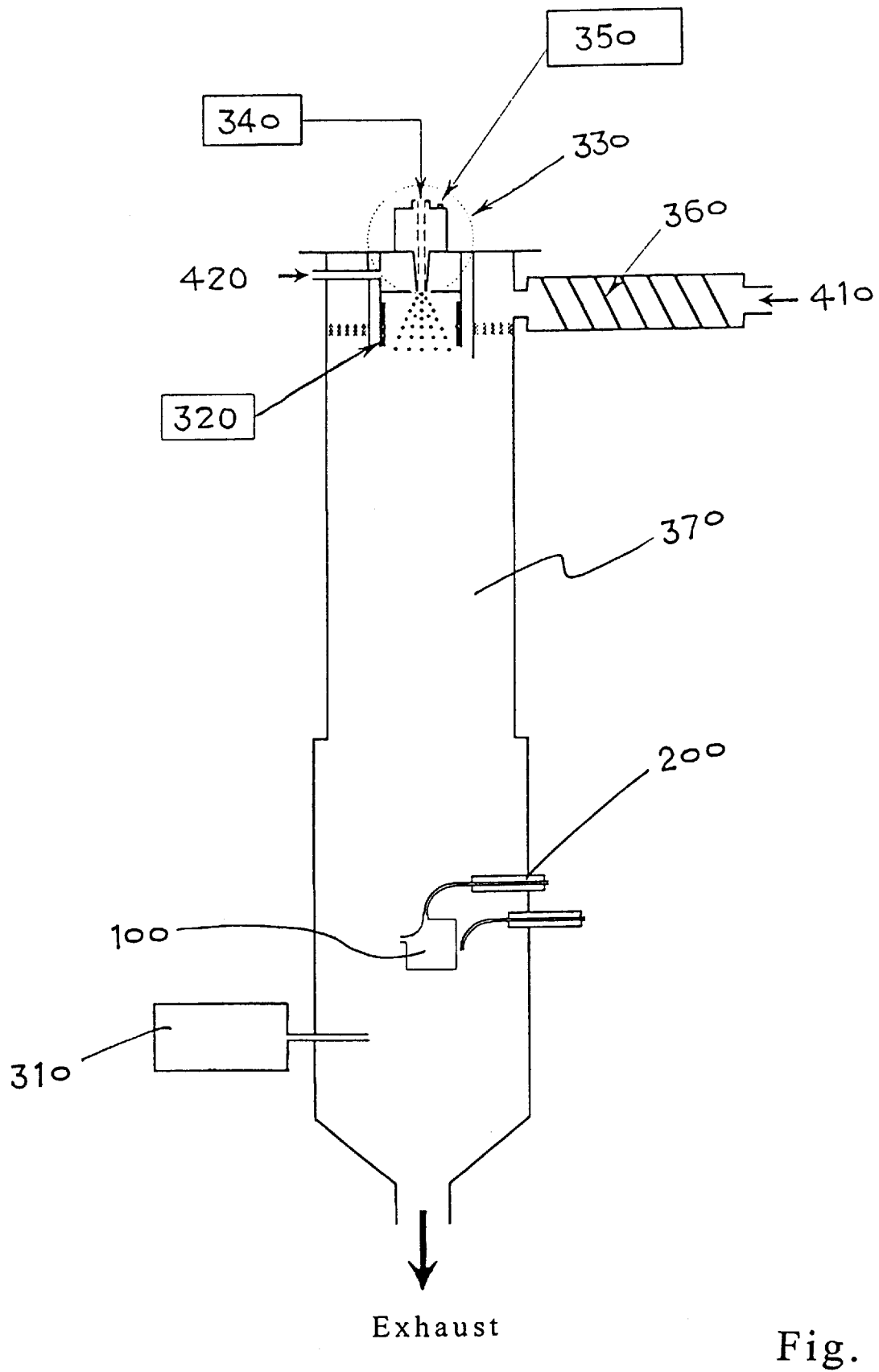
FIG. 8 shows a schematic view of a system layout of the present invention.

The aerosol size-selective sampling system of the present invention comprises, as shown in FIG. 8, a virtual cyclone sampler 100, an aerodynamic particle sizer 200, an aerosol electrometer 310, an aerosol neutralizer 320, an atomizing nozzle 330, a peristaltic pump 340, a power source switch 350, a heating wire 360, a testing chamber 370, an inlet 410 for filtered air, and an extra air inlet 420.

Figure 17:
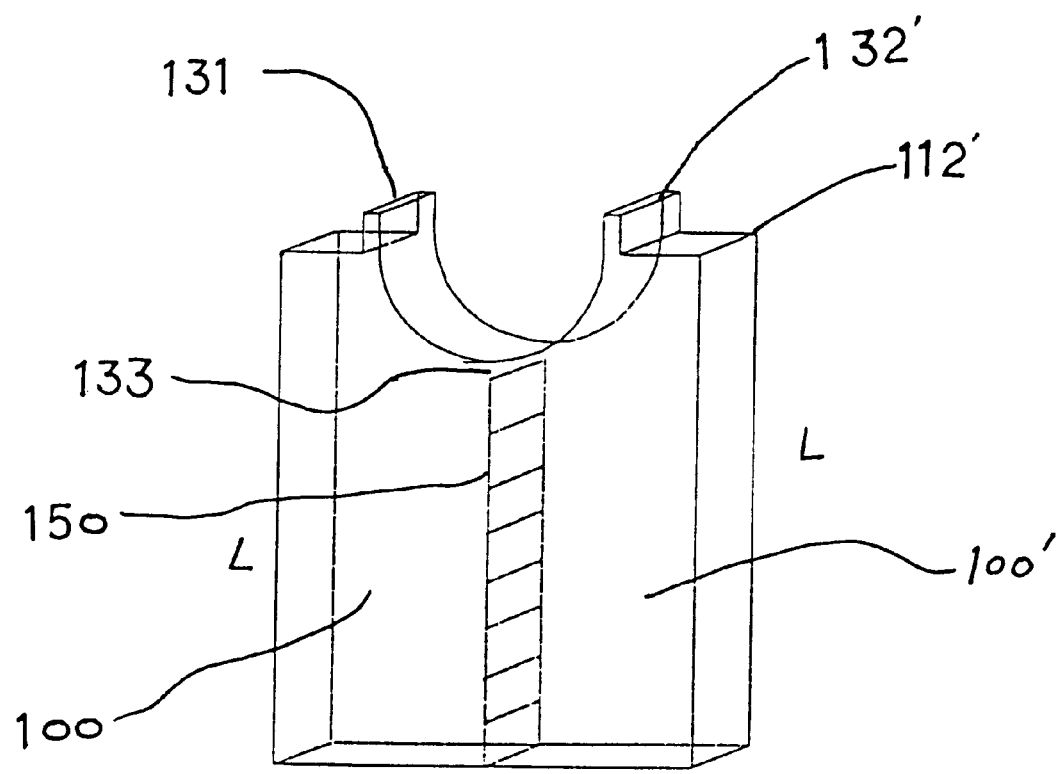
FIG. 17 shows a schematic view of a composite virtual cyclone sampler of the present invention.

The virtual cyclone sampler 100 of the present invention may be used alone or in a combination fashion such that two or three virtual cyclone samplers 100 are interconnected, as shown in FIG. 17. Two virtual cyclone samplers 100 and 100' are separated by a partition 150. Located between the partition 150 and the arcuate surface is a guide slot 133 for communicating the sampler 100 with the sampler 100'. For experimental data of this composite sampler, please refer to the Embodiments 14 and 15.

In taking the sample, a filter cassette may be used, as shown in FIG. 21. The guide slot 132 is a simple planar slot. 500 is a connecting device. 600 is a filter cassette which is connected to a protruded guide slot 131 of the virtual cyclone sampler 100 with the connecting device 500.

The Experimental Method of the Present Invention

1. Generation and Measurement of Aerosol

The experimental system is mainly divided into two portions, which include the particle generation and the particle size measurement. The system layout is shown in FIG. 8. In the process of generating the particle, the peristaltic pump 340 was used in such a manner that the peristaltic pump 340 was controlled and operated by a computer hardware and an operating software. The peristaltic pump 340 was purchased from Cole-Parmer Instrument Co. of the United States, with the pump model number being Model 7550-90, Cartridge Pump Head System. The peristaltic pump 340 was used to transport the solution of potassium sodium tartrate tetrahydrate, PST, which was then atomized by the ultrasonic atomizing nozzle 330 which was purchased from Sono-Tek, Inc. of the United States, with its product model code being Model 8700-60MS & Model 8700-120MS. The atomized solution was diluted by the clean air. Such a mixture was completely dried. About 100 L/min of dry clean diluted air was allowed to pass through the heating tape 360, which was purchased from Glas-Col, U.S.A., before entering the testing chamber 370. The distribution and the concentration of the aerosol were measured by the aerodynamic particle sizer (APS) 200, which was purchased from TSI, Inc. of the United States. In light of the pump restriction in the individual sampler in the experiments, the basic flow of the sampler was set lower than 5 L/min. However, the sampling flow rate of APS was set at about 5 L/min. For this reason, an extra gas was sent into the APS to compensate the difference between the flow rates of the sampler and APS.

The cross-sectional area of the testing chamber was $22 \times 22 = 484$ cm$^2$. The introduced gas was about 102 L/min (diluted air plus repelling air). The wind speed in the testing chamber was calculated to be 3.5 cm/s. Therefore, it was assumed that the testing system was in the state of calm air.

The freshly generated aerosol often carries a considerable amount of electricity, which may affect the stability of the experiment. For this reason, an aerosol neutralizer 320 (Po-210 of 25 mCi made by NRD, Inc. of U.S.A; model P-2001) was disposed under the ultrasonic atomizing nozzle 330 for neutralizing the electricity of the aerosol, so as to attain the so-called "Boltzmann charge equilibrium" state. In the meantime, the aerosol electrometer 310 was disposed in the proximity of the bottom of the testing chamber 370 for monitoring the electrical charge of the particle.

In order to enhance the stability of the experiment, all flows of the system were controlled and monitored by a mass flow controller, which was purchased from Hastings Instrument of the United States. The flow correction was done by an infrared device which was purchased from Gilian Instrument Co. of the United States.

The process of size-selective sampling of aerosol calls for the use of size-selective sampler, a sampling pump, and a collection interface. When the collection interface is a filter paper, the collection efficiency of the sampling process may be expressed by the following number collection efficiency (E) or weight collection efficiency ($E_m$) (Hinds, 1987):

$$E = \frac{N_{in} - N_{out}}{N_{in}} \quad (7)$$

$$E_m = \frac{C_{in} - C_{out}}{C_{in}} \quad (8)$$

wherein:

$N_{in}$ and $N_{out}$ are number concentrations of aerosol entering and penetrating the filter paper, respectively; and $C_{in}$ and $C_{out}$ are weight concentration of aerosol entering or penetrating the filter paper On the other hand, the collection efficiency of the sampling process may be expressed by the penetration rates as follows:

$$P = \frac{N_{out}}{N_{in}} = 1 - E \quad (9)$$

$$P_m = \frac{C_{out}}{C_{in}} = 1 - E_m \quad (10)$$

wherein

P and $P_m$ are the ratios between the aerosol entering the filter paper and the aerosol penetrating the filter paper in number and weight, respectively. $N_{in}$, $N_{out}$, $C_{in}$, $C_{out}$, E and $E_m$ are defined as above.

Similarly, the aerosol penetration rate can be attained by dividing the particle concentrations in upstream and downstream of the sampler, which can be measured by using the APS.

2. Instruments Used in Experiment (1) peristaltic pump, Model 7519-90, Cole Parmer Instrument Co., Niles, Ill., U.S.A.

Two pumps were used in the experiment. The revolving speed of the pumps was 60 RPM. For the transport of the liquid, two kinds of tubes were used. The tube with a smaller diameter was made of a tygon material, with the inner diameter of the tygon tube being 0.19 mm and the liquid flow ranging between 0.007 and 0.4 ml/min. Another tube with a greater diameter was made of a silicon material, with the inner diameter of the silicone tube being 0.90 mm and the liquid flow ranging between 0.09 and 5.4 ml/min. The water was transported in such a manner that a roller-type axle makes contact with a hose, which is then squeezed so as to transport the liquid. This implies that the liquid is transported only at the time when the hose and the axle come in contact with each other. When the axle is in motion, there is an intermittent contact between the hose and the roller such that a pulsation is brought about. The pulsation undermines the stability of the experiment and affects the particle distribution. The pulsation was eliminated in the experiment by means of two Y connectors which were disposed at the entrance and the exit of the axle and were connected with two parallel hoses therebetween. In the meantime, the two cartridges used for fastening the hoses on the roller were in the opposite directions, thereby resulting in the cancellation of pulsation of the two hoses.

(2) ultrasonic atomizing nozzle, Model 8700-60MS & Model 8700-120MS, Sono-Tek, Highland, N.Y., U.S.A.

The nozzle works by means of a piezoelectric transducer, which converts the electrical energy into the mechanical energy for bringing about a high-frequency sound wave for use in smashing the liquid into droplets, which are then dried for use as test particles. The diameter of the liquid droplet is affected by the frequency of the nozzle, the liquid surface tension and the liquid density, with the frequency of the nozzle being the most influential factor. The system of the present invention makes use of two kinds of nozzles, which are different in frequency in that one has a frequency of 60 KHz, and that other one has a frequency of 120 KHz, and further that the minute liquid droplets generated by the nozzles have the median diameters of 32 $\mu$m and 20 $\mu$m respectively. Generally speaking, the diameter distribution of the droplets generated by the ultrasonic atomizing nozzle may be regarded as a logarithmic normal distribution. The aerosol that is formed from the droplets by a drying process may also be presumed as a logarithmic normal distribution. The size of the aerosol particle is determined by two important factors, which are the size of the droplets from which the aerosol is formed by the drying process, and the ratio of the nonvolatile solutes contained in the droplets. This relationship may be expressed by a formula as follows:

$$D_p = (C+I)^{1/3} \times D_d$$

in which $D_p$ stands for the aerosol particle diameter ($\mu$m); C, the volumetric fraction (vol./vol.) of the nonvolatile solutes contained in the solution; I, the volumetric fraction (vol./vol.) of the impurities contained in the solution; and $D_d$, the particle diameter ($\mu$m) of the liquid droplets.

In addition to the factors described above, the size and the distribution of the particles are also dependent on the power magnitude of the ultrasonic atomizing nozzle, as revealed by certain research reports. However, the factor of the power magnitude of the nozzle was negligible in the experiment of the present invention in view of the fact that the powers of the nozzles used in the experiment were set at 6.0 watts (60 KHz) and 4.5 watts (120 KHz) respectively.

(3) Aerodynamic particle sizer, model 3310A, TSI, Inc., St. Paul, Minn., U.S.A.

The diameter and the number concentration of the aerosol in $\mu$m level were measured by the aerodynamic particle sizer (APS). The measuring technique is based on the principle that the particles of different sizes are accelerated differently. The measuring technique was carried out in the experiment by guiding the particles to pass through an accelerated flow field and two parallel laser beams such that the time of flight (TOF) of the particles through the laser beams was measured. The aerodynamic diameter ($D_{ae}$) of the aerosol was calculated on the basis of the measurement data. The measurable particle diameter was in the range of 0.8–30 $\mu$m.

The aerodynamic particle sizer is not suitable for use in measuring the aerodynamic diameter of an aerosol, when the concentration of the aerosol is high. The reason is that the so-called "coincidence errors" are prone to take place at the time when an excessive amount of particles are guided to pass through the laser beams concurrently. As a result of the coincidence errors, the measurement can be distorted by the phenomena of underestimation and phantom particle (Heitbrink, et al., 1991, Heitbrink and Baron, 1992). However, the coincidence errors can be avoided by controlling the concentration of the particles that are introduced into the testing chamber.

(4) Aerosol neutralizer, Po-210 (Model P-2001, NRD, Inc., Grand Island, N.Y.).

The polonium 210 is a radioactive material and was used in the experiment of the present invention to neutralize the electric charges of the particles in light of the polonium 210 being capable of giving off $\alpha$-particle in the course of its decay so as to disintegrate the air molecules into the positive ions and the negative ions, which act to neutralize the electrically-charged particles by adhering to the surface of the particles. The half life of the polonium 210 is 138 days.

(5) Aerosol electrometer, Model 3068, TSI, Inc., St. Paul, Minn., U.S.A.

The aerosol electrometer is mainly formed of an electric current meter and a Faraday cup which is provided therein with a filter paper. As particles are trapped by the filter paper, the Faraday cup is electrically charged by the electrical charge of the aerosol. The electric current is then measured by the electric current meter of the aerosol electrometer. The value of the electric charge of the aerosol is then converted from the measured value of the electric current of the Faraday cup. As a result, the equilibrium of electric charge of the aerosol in the testing chamber can be thus monitored.

In the following embodiments, the virtual cyclone samplers of the present invention were made of an acrylic material.

The experiments were intended to investigate the sampling flow rate (Q), the radius (R) and the angle ($\Theta$) of the current making a turn, the width ratio between the inlet ($W_i$) and the outlet ($W_o$), and the length (L), etc., as shown in FIG. 7.

COMPARISON EXAMPLES 1–4

Potassium sodium tartrate tetrahydrate solution was atomized by the ultrasonic atomizing nozzles to form solid particles having two different diameter distributions. The atomization was carried out in the presence of the neutralizer, Po-210 of 25-mCi, and a humidifying system for adjusting various humidity conditions. The aerodynamic diameter and the number concentration of the aerosol were measured by the aerodynamic particle sizer (APS, Model APS 3310A, TSI, Inc.). The size-selective samplers were the conventional 10 mm nylon cyclone, SKC cyclone, multi-port cyclone, and BB cyclone. The aerosol penetration curves of the aerosol having a smaller diameter distribution (count median diameter (CMD)=3.5 $\mu$m, GSD=1.3, concentration=4.6 mg/m$^3$) at the beginning of the sampling and after a 3-hour elapsed time are shown in FIGS. 3, 4, 5 and 6.

The experimental results shown in FIGS. 3–6 indicate that the particle collecting efficiency curves of the four cyclones change when the elapsed time increases. For example, after a 3-hour elapsed time the penetration rates of an aerodynamic diameter of 3.97 $\mu$m with the 10 mm nylon cyclone, the SKC cyclone and the BB cyclone drop to 30% from the initial 50%. A relatively smaller change (50%→40%) in the penetration rates was observed when the multi-port cyclone was used. However, under the circumstance that the particles have a greater diameter distribution (CMD=7.4 $\mu$m, GSD= 1.5, concentration=15.1 mg/m$^3$), the particle collecting efficiency curves (not shown in the drawings) of all cyclones, except the SKC cyclone, remain almost unchanged. It is therefore readily apparent that the rate of deposit of particles in the tube wall is dependent on the wind speed at the inlet of the cyclone and the size of the particles. For this reason, a crucial issue confronting the size-selective samplers is to reduce the load of the particles.

Embodiments 1–11

The experiments were carried out by using the virtual cyclone sampler of the present invention. The method for carrying out the experiments is the same as that which was described above. The following table contains values of parameters of the virtual cyclone samplers of the present invention.

| Embodiment | R | $W_i$ | $W_o$ | L | Q (L/min) |
|---|---|---|---|---|---|
| 1 | 7.5 | 1.0 | 0.8 | 21 | 3.30 |
| 2 | 10 | 1.0 | 0.8 | 13 | 3.30 |
| 3 | 10 | 1.0 | 0.8 | 21 | 2.60 |
| 4 | 10 | 1.0 | 0.8 | 21 | 3.30 |
| 5 | 10 | 1.0 | 0.8 | 21 | 4.23 |
| 6 | 10 | 1.0 | 0.8 | 31 | 3.30 |
| 7 | 10 | 1.0 | 0.8 | 39 | 3.30 |
| 8 | 10 | 1.0 | 0.8 | 92 | 3.30 |
| 9 | 19 | 1.0 | 0.8 | 21 | 2.02 |
| 10 | 19 | 1.0 | 0.8 | 21 | 2.82 |
| 11 | 19 | 1.0 | 0.8 | 21 | 3.30 |

The density of the solid particles of potassium sodium tartrate tetrahydrate used in all experiments was 1.79 mg/cm$^3$. In order to prevent the erroneous measurement of the particle diameter by the aerodynamic particle sizer due to the factor of particle density, the particle diameters measured by the instrument in the experiment were replaced by the results of the first degree correction, so as to prevent the size-selective curves of the sampler from deviating from their original true values.

Figure 9:
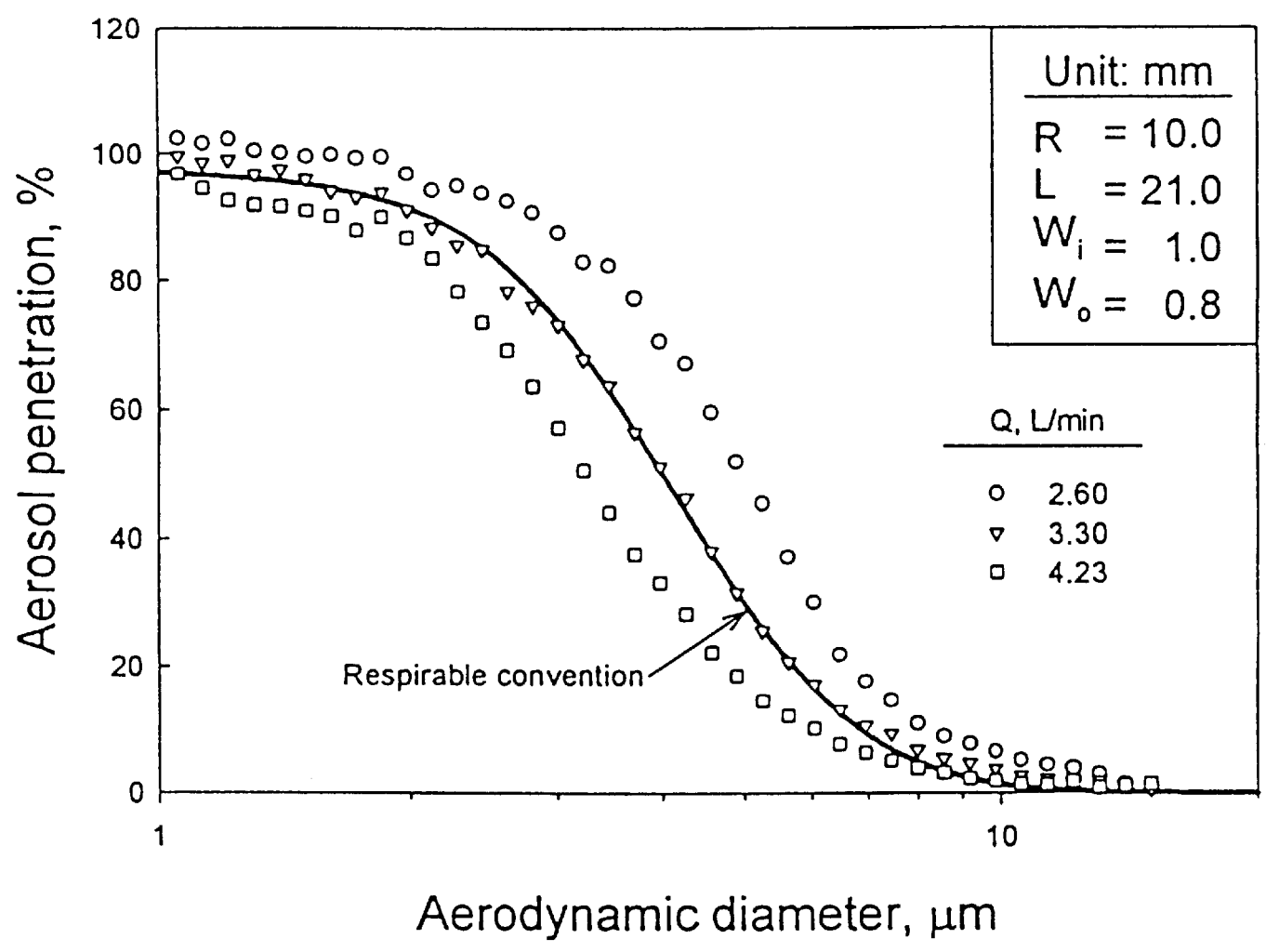

The experimental data of the third embodiment, the fourth embodiment and the fifth embodiment of the present invention are presented in FIG. 9 for explaining the relationship between the sampling flow rate (Q) and the sampling efficiency. In FIG. 9, the black bold solid line is the size-selective curve of CEN/ISO/ACGIH relative to the respirable aerosol. The data shown from the right to the left are size-selective results under the circumstance that the sampling flow rates are 2.60, 3.30, and 4.23 L/min. When the sampling flow rate was increased from 2.60 L/min to 4.23 L/min, the 50% cut-off diameter of the sampler was reduced from 5 μm to about 3 μm. When the flow was 3.30 L/min., the curve conform to the respirable convention regardless of the 50% interception diameter or the slope.

Figure 10:
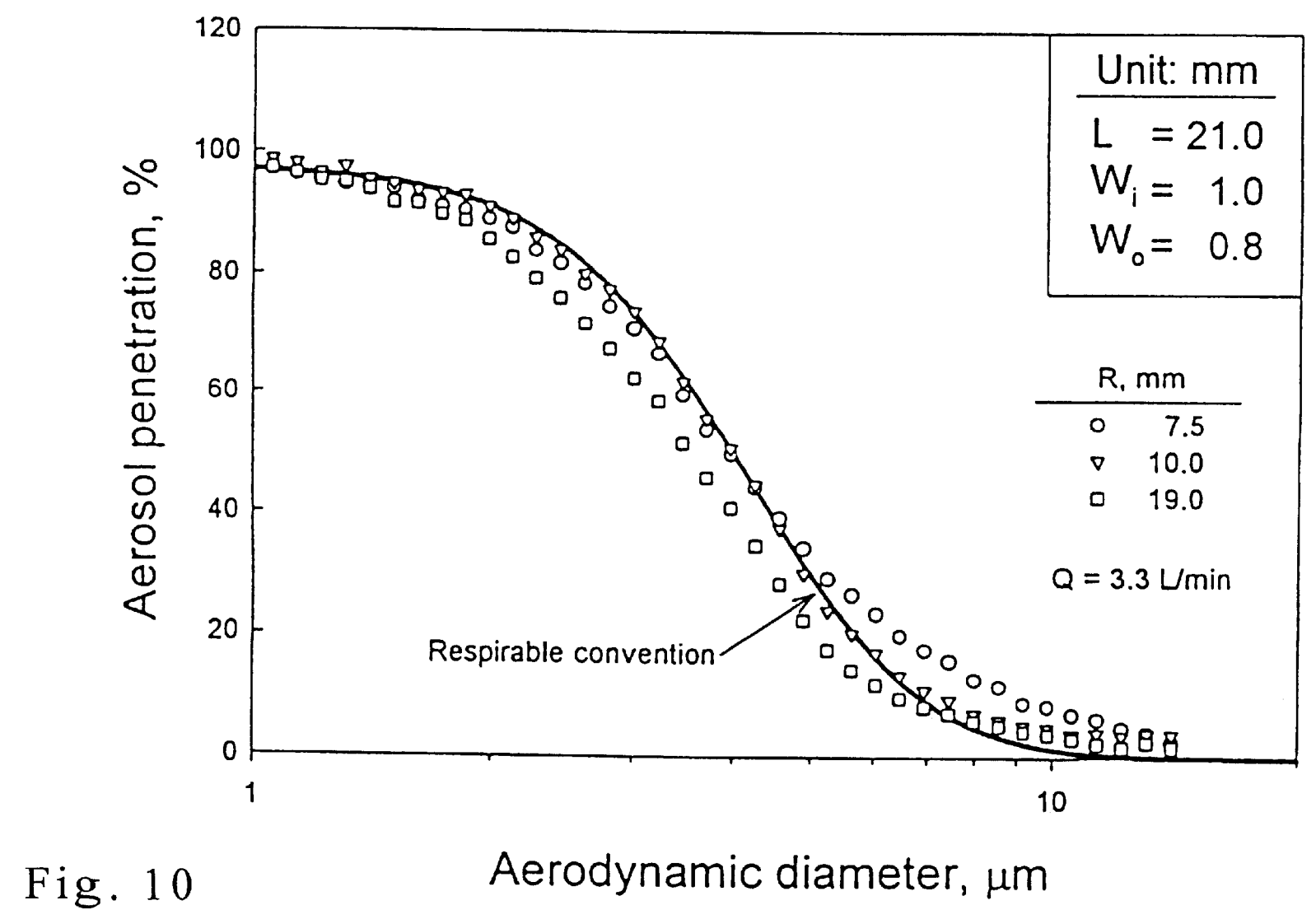

The experimental data of the first, the fourth and the ninth embodiments of the present invention are shown in FIG. 10 for explaining the relationship between the turning radius (R) of the current and the sampling efficiency. Under the circumstance that the remaining parameters are the same, and that R is reduced to 7.5 mm, the residence time of the particles in the sampler may be relatively short, so that the efficiency for collecting the particles having a greater diameter of the size-selective sampler is reduced. As a result, the efficiency curve is relatively less steep with respect to particles having a greater aerodynamic diameter. However, the inclination of the efficiency curve is not greatly affected.

Figure 11:
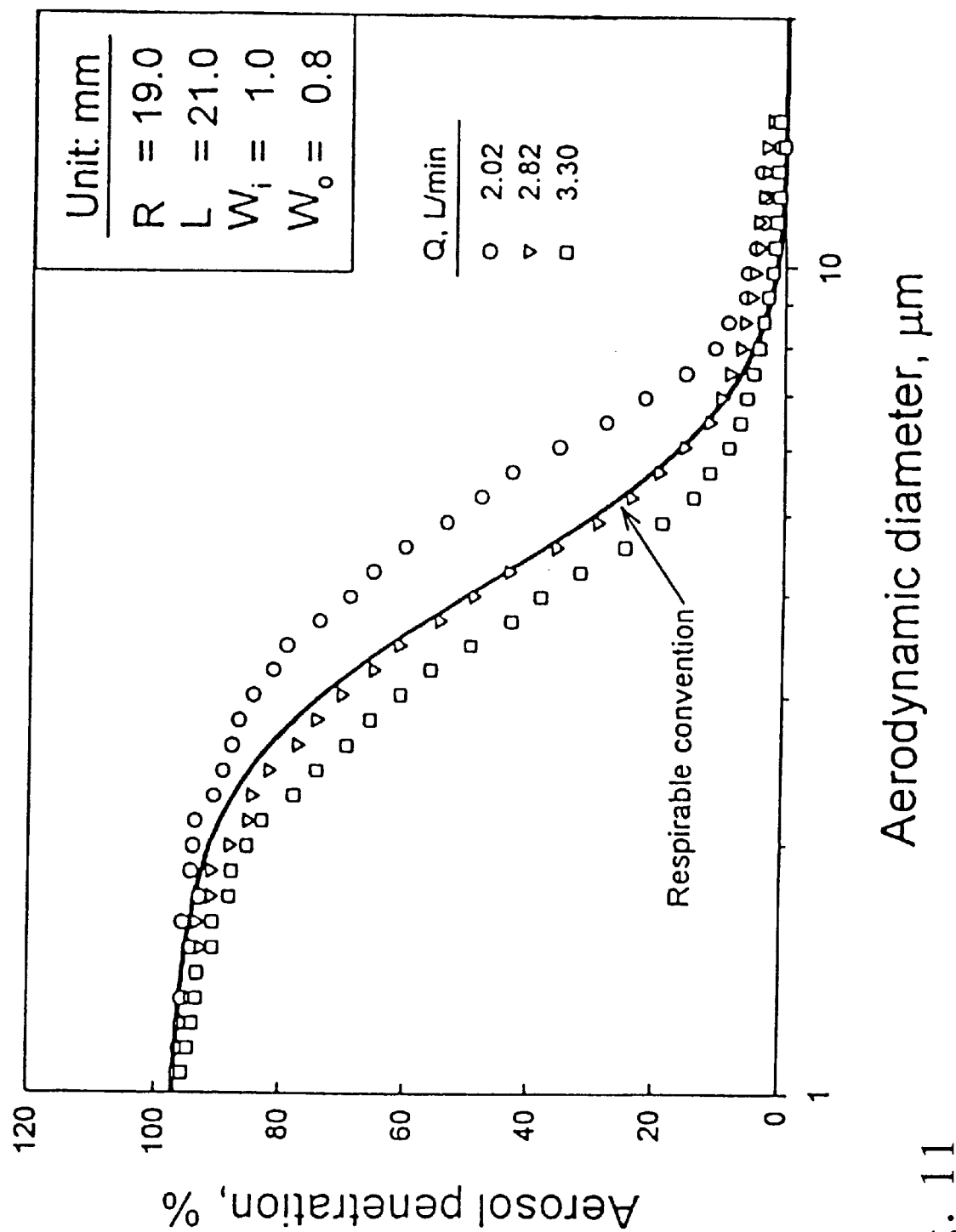

The experimental data of the ninth embodiment, the tenth embodiment, and the eleventh embodiment of the present invention are presented in FIG. 11. The efficiency curve of the virtual cyclone sampler may also be forced to conform to the respirable convention by changing the flow rate. The results are shown in FIG. 11. When the sampling flow rate is reduced to 2.82 L/min from 3.3 L/min, there is an agreement between the two. However, there is a slight difference between the collecting efficiency and the conventional curve for the particles having a aerodynamic diameter greater than 7 μm.

Figure 12:
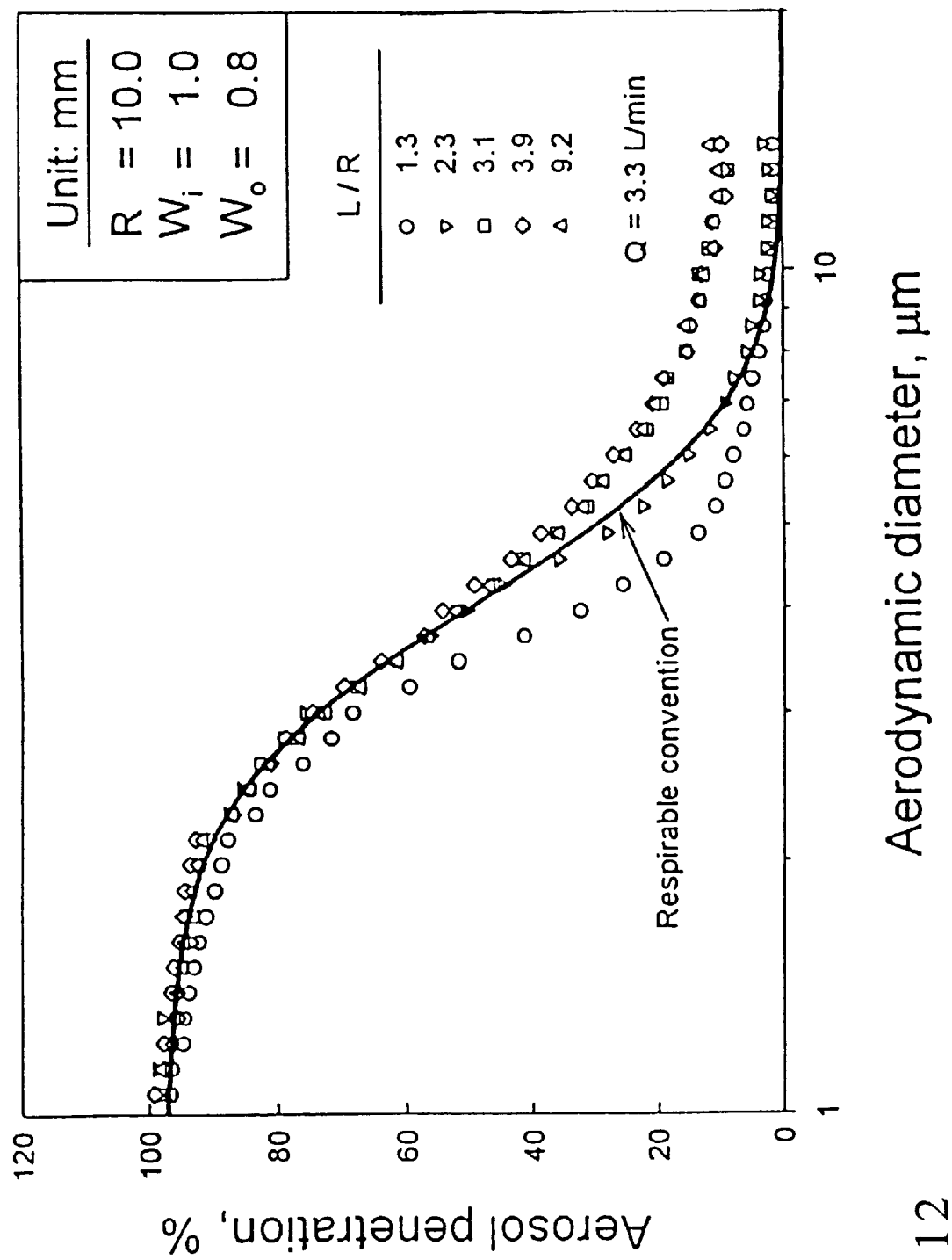

The experimental data of the second embodiment, the fourth embodiment, the sixth embodiment, the seventh embodiment, and the eighth embodiment of the present invention are shown in FIG. 12. The length (L) of the virtual cyclone sampler is shown to be a factor affecting the size-selective efficiency of the sampler. As shown in FIG. 12, when the distance between the bottom of the recirculating chamber and the outlet of the sampler is reduced to a certain extent, the inclination of the efficiency curve of the sampler becomes relatively steep. If the length (L) of the sampler is gradually increased, the inclination of the efficiency curve becomes gradually less steep. However, if the length (L) of the sampler is increased to a certain extent, the efficiency curve is not affected. According to the embodiments 1–11 of the present invention, the dimension of the optimal virtual cyclone sampler is as follows:

R=10 mm, $W_i$=1.0 mm, $W_o$=0.8 mm, L=21 mm, F=3.3 L/min.

Embodiments 12–13:

The load experiments were conducted by using the particles of potassium sodium tartrate tetrahydrate (PST). The experimental conditions and results are shown in the following table.

Figure 13:
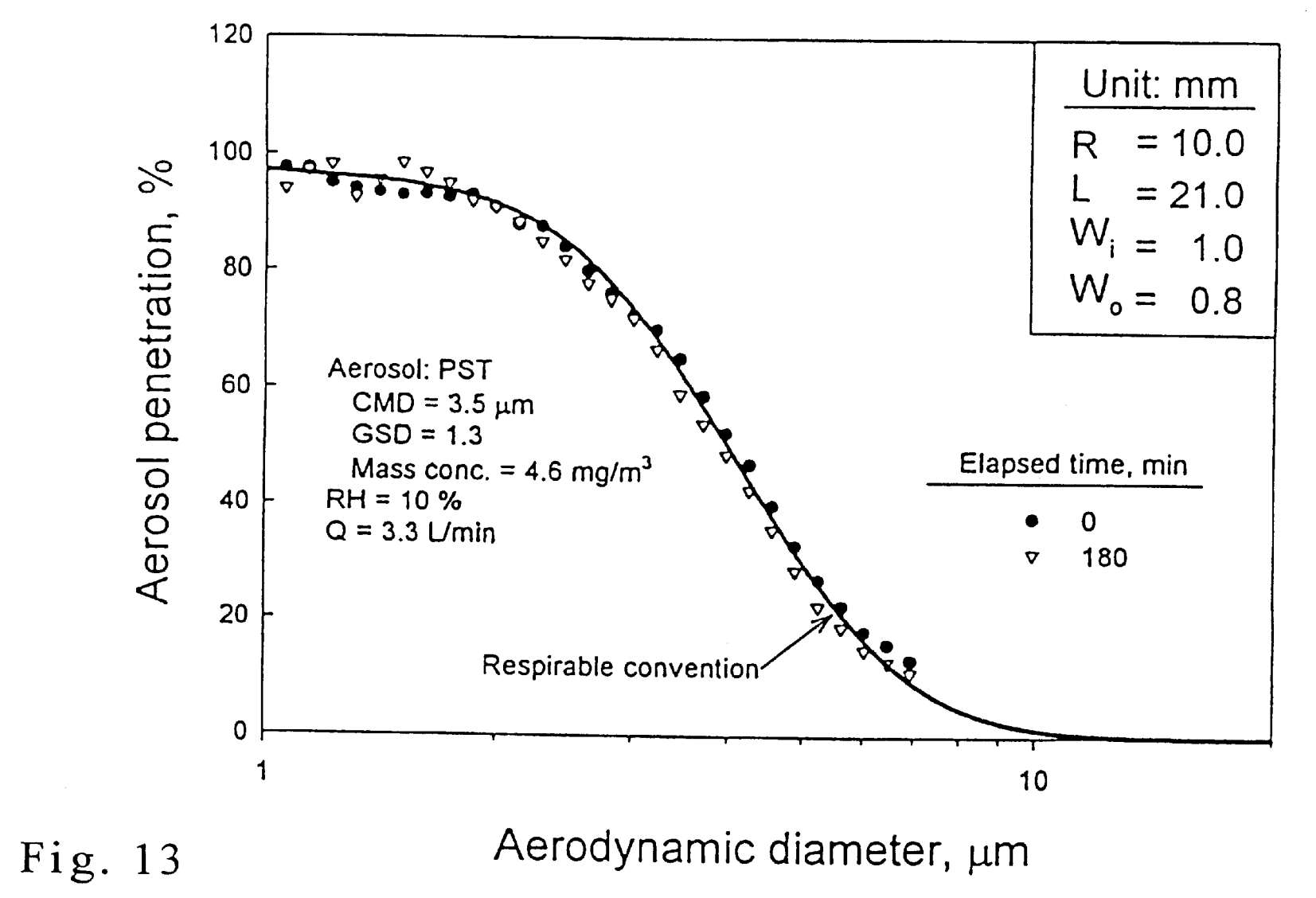
Figure 14:
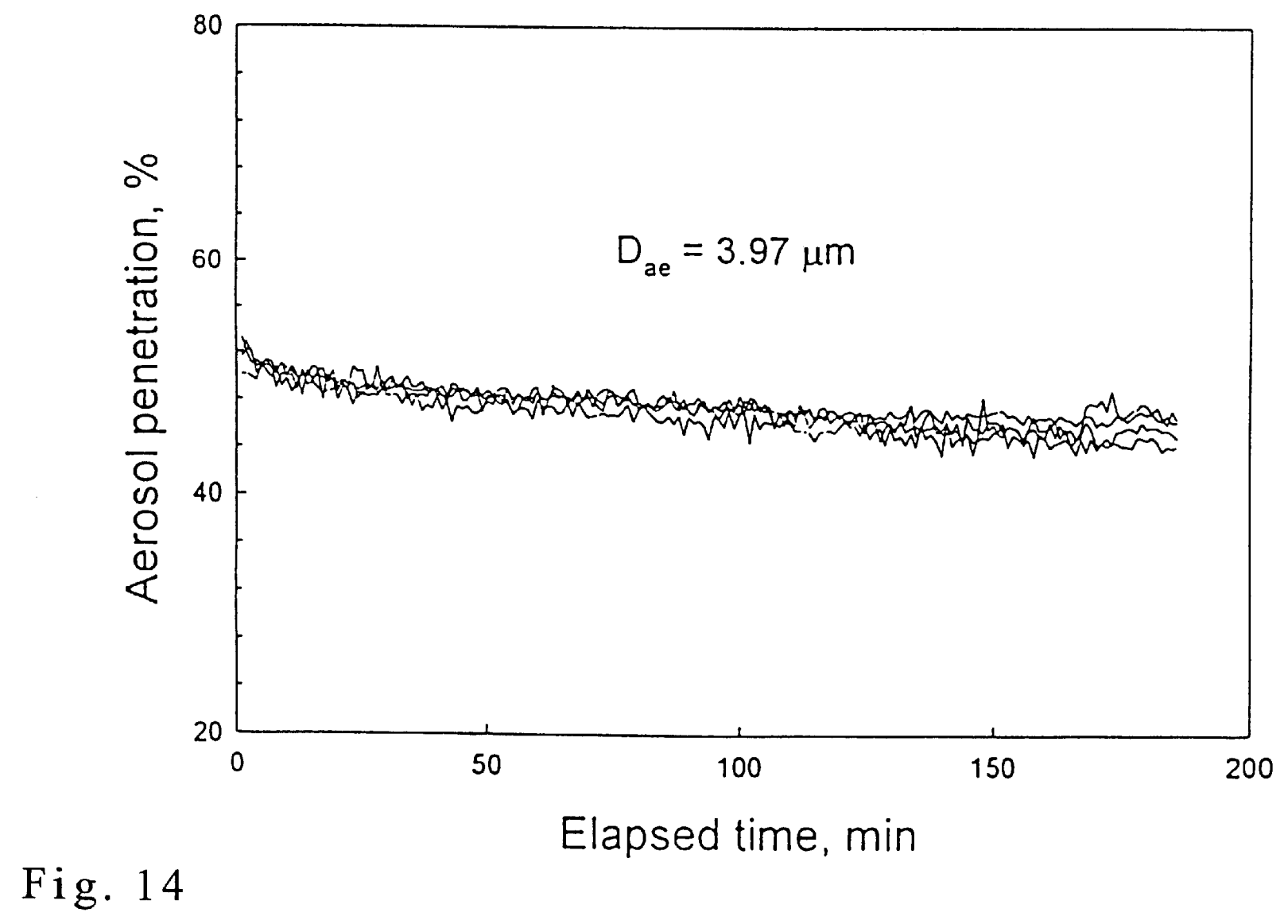
Figure 15:
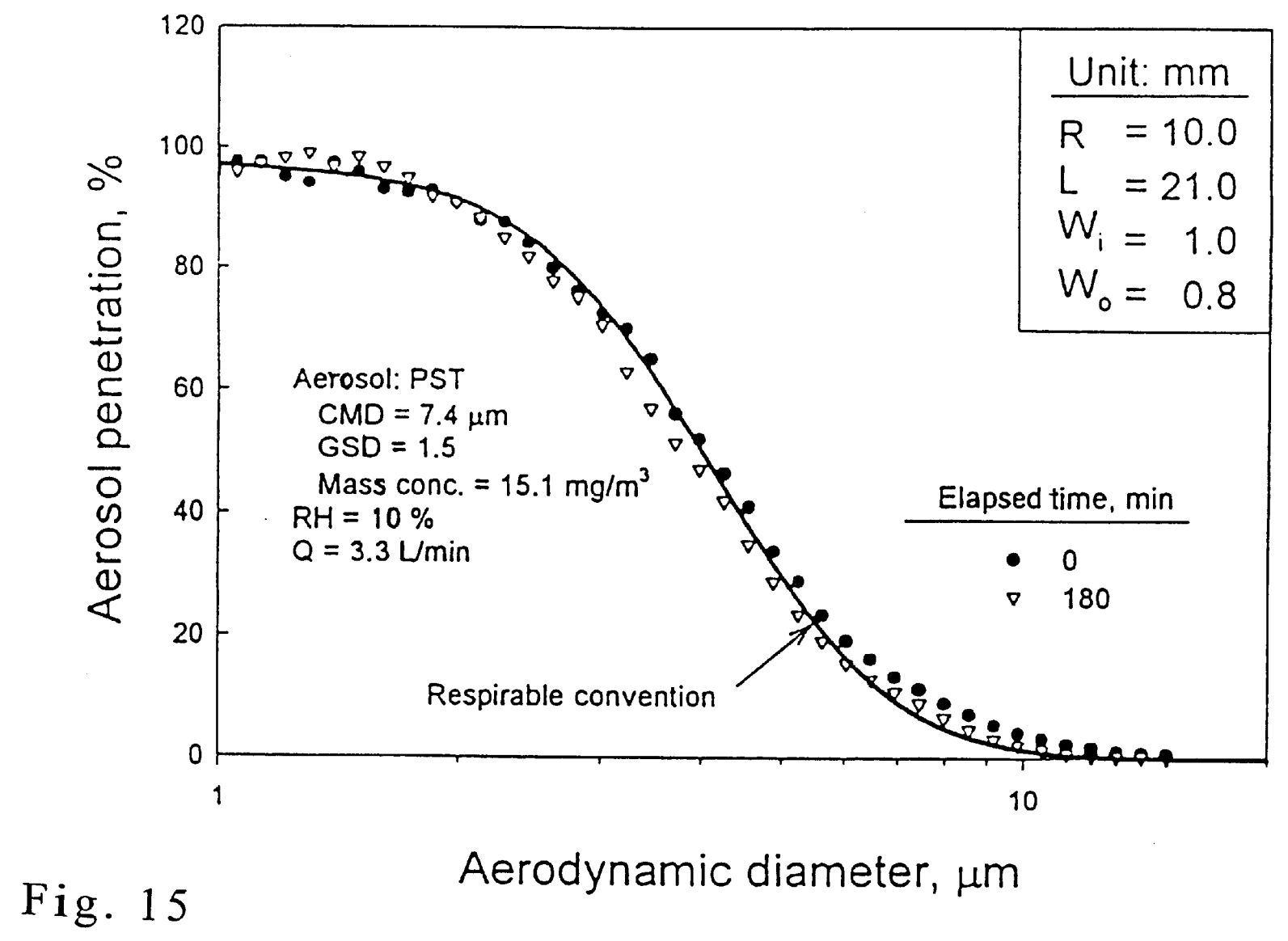
Figure 16:
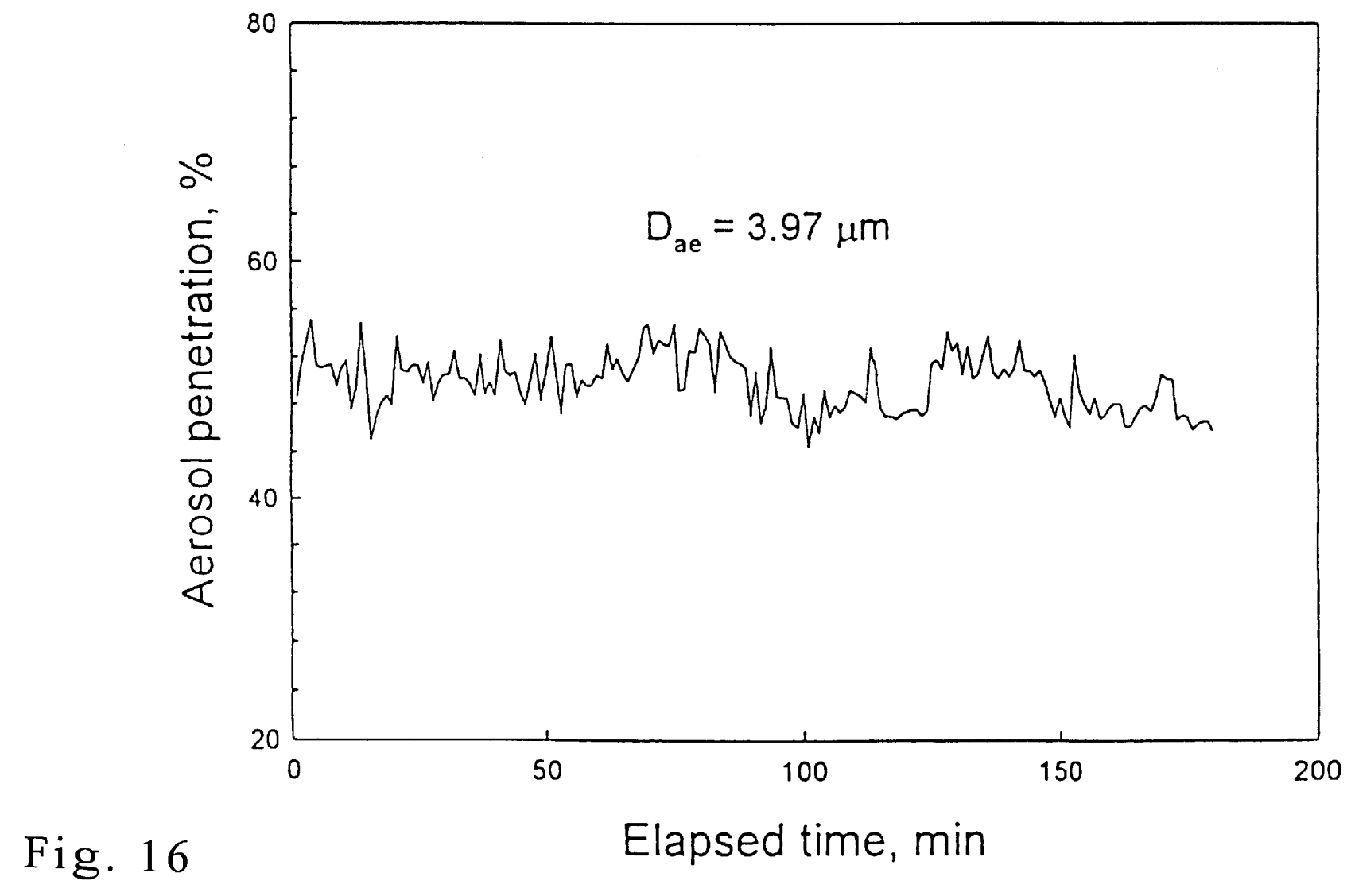

| | Embodiment 12 | Embodiment 13 |
|---|---|---|
| Aerosol | PST | PST |
| CMD | 3.5 μm | 7.4 |
| GSD | 1.3 | 1.5 |
| Weight concentration | 4.6 mg/m$^3$ | 15.1 mg/m$^3$ |
| Relative humidity | 10% | 10% |
| Q | 3.3 L/min | 3.3 L/min |
| R | 10.0 | 10.0 |
| L | 21.0 | 21.0 |
| $W_i$ | 1.0 | 1.0 |
| $W_o$ | 0.8 | 0.8 |
| Aerosol penetration curves at onset and at 3-hour elapsed time | FIG. 13 | FIG. 15 |
| Change in penetration rate | FIG. 14 | FIG. 16 |

The results of the experiments show that the efficiency curves did not change obviously after 3-hour load experiments, under the circumstance that the relative humidity was set constantly at 10%, and regardless of the diameter distribution of the particle size, as shown in FIGS. 13 and 15. For example, the penetration rate of the particle having an aerodynamic diameter of 3.97 μm was kept at about 50% as shown in FIG. 14. The reproducibility was also good. However, in FIG. 16, the number of the particles used for testing was relatively small, and this may cause the variation more serious.

It is therefore concluded that the virtual cyclone samplers of the present invention conform to the requirements of the internationally-defined respirable curve. In terms of the effect of the particle load, a considerable improvement has been attained on the virtual cyclone sampler of the present invention in comparison with the existing samplers, such as 10 mm nylon cyclone, SKC cyclone, multi-port cyclone, BB cyclone, etc.

Embodiment 14:

A composite virtual cyclone sampler was used in this embodiment, as shown in FIG. 17. The method for carrying out the experiment of this embodiment the same as that which was used in EMBODIMENTS 1–11 in which a single virtual cyclone sampler was used. The specifications of the composite virtual cyclone sampler are as follows: R=10 mm, $W_i$=1.0 mm, $W_o$=0.6 mm, L=75 mm. The distance between the partition 150 and the arcuate surface was 0.8 mm (the guide slot 133), and Q=3.6 L/min. The aerosol penetration rate curve is shown in FIG. 18.

Embodiment 15:

A composite virtual cyclone sampler was used. The specifications of the composite virtual cyclone sampler are R=10 mm, $W_i$=1.0 mm, $W_o$=0.6 mm, and L=75 mm. The distance between the partition 150 and the arcuate surface was 0.8 mm. The distance is corresponding to the width of the guide slot 133, as shown in FIG. 17. The aerosol was formed of PST, with CMD=3.5 μm, GSD=1.3, weight concentration=4.6 mg/m³, relative humidity=10%, Q=3.6 L/min. The aerosol penetration rate curves are shown in FIG. 19. The change in penetration rate of the aerosol having an aerodynamic diameter ($D_{ae}$) against elapsed time is shown in FIG. 20. According to EMBODIMENTS 14 and 15, when two virtual cyclone samplers are connected in symmetry, the size-selective efficiency curve conform to the respirable convention with respect to the 50% cut-off particle diameter and slope, especially for the aerosol having 10 an aerodynamic diameter greater than 7 μm, as shown in FIG. 18. Similarly, the particle load does not cause the size-selective efficiency curve to deviate, as shown in FIGS. 19 and 20.

In actual sampling of occupation hygiene application, the virtual cyclone sampler of the present invention has a rectangular outlet may cause a problem in connecting with the outside sampling devices. However, a simple connector will be sufficient to connect the rectangular outlet of the virtual cyclone sampler of the present invention to the widely used 37 mm filter paper cassette without developing a new filter cassette. The details thereof is illustrated in FIG. 21.

4. Conclusion and Discussion

One of the objectives of the present invention is to develop a personal sampler capable of attaining a respirable curve conforming completely to the current internationally-defined respirable curve. The reliability of the experiment is dependent on the accuracy in measurement of the particle diameter. The density of the solid particles of potassium sodium tartrate tetrahydrate used in all experiments was 1.79 mg/cm³. In order to prevent the erroneous measurement of the particle diameter by the aerodynamic particle sizer (APS) due to the factor of the particle density, the particle diameters measured by the instrument in the experiment were replaced by the results of the first degree correction, so as to prevent the size-selective efficiency curves of the sampler from deviating from their original true values.

TABLE 1

| | Unit: mm | | | |
|---|---|---|---|---|
| Sampler | R | $W_1$ | $W_o$ | L |
| A | 7.5 | 1.0 | 0.8 | 21 |
| B | 10 | 1.0 | 0.8 | 13 |
| | | | | 21 |
| | | | | 31 |
| | | | | 39 |
| | | | | 92 |
| C | 19 | 1.0 | 0.8 | 21 |

The experiment used the parameter values which are contained in Table 1. For the convenience of describing the experiment, the virtual cyclone samplers are divided into three categories on the basis of the size of the turning radius R of the air flow, A (R=7.5 mm), B (R=10 mm), and C (R=19 mm), and other variables ($W_i$=1.0 mm, $W_o$=0.8 mm, L=21 mm) remain the same. Each sampler has a recirculating chamber with a changeable length (L).

The size-selective sampling efficiency of the virtual cyclone sampler was observed on the basis of the sampling flow rate. As shown in FIG. 9, the black bold solid line is the size-selective efficiency curve of CEN/ISO/ACGIH relative to the respirable aerosol. The data shown from the right to the left are size-selective sampling results under the circumstance that the sampling flow rates are 2.60, 3.30, and 4.23 L/min. When the sampling flow rate was increased from 2.60 L/min to 4.23 L/min, the 50% cut-off diameter of the sampler was reduced from 5 μm to about 3 μm. When the flow rate was 3.30 L/min, the curves conform to the internationally-defined respirable curve regarding to the 50% cut-off diameter or the slope.

The relationship between the turning radius (R) of the current and the sampling efficiency is shown in FIG. 10. Under the circumstance that the remaining parameters are the same, and that R is reduced to 7.5 mm, the residence time of the particles in the sampler may be relatively short to reduce the efficiency of the size-selective sampler to collect the particles having a greater diameter. As a result, the efficiency curves are relatively less steep. However, the inclination of the efficiency curve is not greatly affected. The virtual cyclone sampler C may conform to the internationally-defined respirable curve by changing the flow rate. The results are shown in FIG. 11. When the sampling flow rate is reduced to 2.82 L/min from 3.3 L/min, there is an agreement between the two. However, there is a slight difference between the collecting efficiency and the internationally-defined respirable curve for the particles having a diameter greater than 7 μm.

The length (L) of the virtual cyclone sampler is shown to be a factor affecting the size-selective efficiency of the sampler. Let's take the sampler B as an example. As shown in FIG. 12, when the distance between the bottom of the recirculating chamber and the outlet of the sampler is reduced to a certain extent, the slope of the efficiency curve of the sampler becomes relatively steep. If the length (L) of the sampler is gradually increased, the inclination of the efficiency curve becomes gradually less steep. However, if the length (L) of the sampler is increased to a certain extent, the efficiency curve is not affected.

According to Embodiments 1–11 of the present invention, the optimum specifications of the virtual cyclone sampler are: R=10 mm, $W_i$=1.0 mm, $W_o$=0.8 mm, L=21 mm, and Q=3.3 L/min.

Another objective of the present invention is to provide a virtual cyclone sampler capable of overcoming the drawback of the curve deviation which is caused by the accumulation of particles in the size-selective sampler. For this reason, the load experiments were carried out by using two kinds of solid particles of potassium sodium tartrate tetrahydrate, which were a large PST (CMD=7.4 μm, GSD= 1.5, weight concentration=15.1 mg/m³) and a small PST (CMD=3.5 μm, GSD=1.3, weight concentration=4.6 mg/m³). The results of the experiments show that the size-selective efficiency curves did not change obviously after 3-hour load experiments, under the circumstance that the relative humidity was set constantly at 10%, and regardless of the diameter distribution of the particle size, as shown in FIGS. 13 and 15. For example, the penetration rate of the particle having an aerodynamic diameter of 3.97 μm was kept at about 50%. The reproducibility was also good. However, in FIG. 16, the number of the particles used in the experiment was relatively small, and the variation was more serious.

It is therefore readily apparent that the virtual cyclone samplers of the present invention conform to the requirements of the internationally-defined respirable curve. In terms of the effect of the particle load, a considerable improvement has been attained on the virtual cyclone sampler of the present invention in comparison with the existing samplers, such as 10 mm nylon cyclone, SKC cyclone, multi-port cyclone, BB cyclone, etc.

As shown in Embodiments 14 and 15, two virtual cyclone samplers were used in such a manner that the two virtual cyclone samplers are connected in symmetry. The size-selective cure at 50% cut-off particle diameter and slope conform to the requirements, especially for the aerosol having a particle diameter greater than 7 μm, as shown in FIG. 18. Similarly, the particle load does not cause the size-selective efficiency curve to deviate, as shown in FIGS. 19 and 20. In actual sampling of occupation hygiene application, the rectangular outlet of the virtual cyclone sampler of the present invention can be connected with a simple connector to the existing 37 mm filter paper cassette without having to develop a new filter paper cassette. The details of the sampling system are shown in FIG. 21.

What is claimed is:

1. A virtual cyclone sampler comprising a container having a hollow, substantially rectangular body, said container being provided with a substantially arcuate surface which is formed by chamfering a boundary edge of two adjacent planes of said hollow substantially rectangular body and covering the resulting opening with a substantially arcuate plane, and said container further provided with two guide slots located respectively at junctions of said substantially arcuate surface and said two chamfered adjacent planes, so that said two guide slots can be used to guide gas or airborne particles to flow into and out of said container.

2. The virtual cyclone sampler as defined in claim 1, wherein said container is a hollow rectangular body having an arcuate surface.

3. The virtual cyclone sampler as defined in claim 2, wherein said two guide slots are rectangular slits conforming to said hollow rectangular body.

4. The virtual cyclone sampler as defined in claim 3, wherein one of said two guide slots is provided with a protruded wall circumventing said rectangular slits.

5. The virtual cyclone sampler as defined in claim 4, wherein said hollow rectangular body has a length (L) ranging between 10 and 100 mm, and a width (W) ranging between 10 and 100 mm; and wherein said rectangular silts have a depth equal to a depth (AB) of said hollow rectangular body, and a width ($W_i$, $W_o$) ranging between 0.4 and 1.6 mm.

6. The virtual cyclone sampler as defined in claim 5, wherein said arcuate surface has a radius (R) ranging between 5 and 25 mm, said radius being smaller than the length (L) and the width (W) of said hollow rectangular body.

7. The virtual cyclone sampler as defined in claim 6, wherein said length (L) of said hollow rectangular body ranges between 13 and 92 mm, said width (W) of said hollow rectangular body ranges between 13 and 92 mm; wherein said width ($W_i$, $W_o$) of said rectangular slits ranges between 0.5 and 1.2 mm; and wherein said radius (R) of said arcuate surface ranges between 7.5 and 19 mm.

8. The virtual cyclone sampler as defined in claim 7, wherein said length (L) of said hollow rectangular body is equal to said width (W) of said hollow rectangular body and ranges between 15 and 25 mm; wherein said width ($W_i$, $W_o$) of said rectangular slits ranges between 0.6 and 1.0 mm; and wherein said radius (R) of said arcuate surface ranges between 8 and 12 mm.

9. A composite virtual cyclone sampler formed of two virtual cyclone samplers as defined in claim 1, wherein said two virtual cyclone samplers are connected in symmetry such that two guide slots of each of said two virtual cyclone samplers are connected with each other, and thus said hollow, substantially rectangular bodies of said two virtual cyclone samplers are in communication with one another through said two connected guide slots of each of said two virtual cyclone samplers.

10. The composite virtual cyclone sampler as defined in claim 9, where each of said containers of said two virtual cyclone samplers is a hollow rectangular body having an arcuate surface.

11. The composite virtual cyclone sampler as defined in claim 10, wherein said two connected guide slots of each of said two virtual cyclone samplers are rectangular slits conforming to respective said hollow substantially rectangular bodies of said two virtual cyclone samplers.

12. The composite virtual cyclone sampler as defined in claim 11, wherein said virtual cyclone samplers have a length (L) ranging between 20 and 80 mm, and a width (W) ranging between 35 and 50 mm; and wherein said arcuate surface has a radius (R) ranging between 7.5 and 19 mm.

* * * * *